(12) United States Patent
Qiao et al.

(10) Patent No.: US 11,478,169 B2
(45) Date of Patent: Oct. 25, 2022

(54) ACTION RECOGNITION AND POSE ESTIMATION METHOD AND APPARATUS

(71) Applicant: HUAWEI TECHNOLOGIES CO., LTD., Guangdong (CN)

(72) Inventors: Yu Qiao, Shenzhen (CN); Wenbin Du, Shenzhen (CN); Yali Wang, Shenzhen (CN); Lihui Jiang, Shenzhen (CN); Jianzhuang Liu, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 337 days.

(21) Appl. No.: 16/846,890

(22) Filed: Apr. 13, 2020

(65) Prior Publication Data

US 2020/0237266 A1    Jul. 30, 2020

Related U.S. Application Data

(63) Continuation of application No. PCT/CN2018/110078, filed on Oct. 12, 2018.

(30) Foreign Application Priority Data

Oct. 13, 2017    (CN) .......................... 201710955087.1

(51) Int. Cl.
*A61B 5/11* (2006.01)
*A61B 5/00* (2006.01)
(Continued)

(52) U.S. Cl.
CPC .......... *A61B 5/1128* (2013.01); *A61B 5/1114* (2013.01); *A61B 5/1116* (2013.01);
(Continued)

(58) Field of Classification Search
CPC ... A61B 5/1114; A61B 5/1116; A61B 5/1127; A61B 5/1128; A61B 5/4528;
(Continued)

(56) References Cited

U.S. PATENT DOCUMENTS 6,681,031 B2    1/2004   Cohen et al.
8,345,984 B2    1/2013   Ji et al.
(Continued)

FOREIGN PATENT DOCUMENTS

CN    104123007 A    10/2014
CN    104200197 A    12/2014
(Continued)

OTHER PUBLICATIONS

Extended European Search Report issued in Application No. 18866516.0 dated Oct. 9, 2020, 12 pages.
(Continued)

*Primary Examiner* — Farzana Hossain
(74) *Attorney, Agent, or Firm* — Fish & Richardson P.C.

(57) ABSTRACT

Action recognition methods are disclosed. An embodiment of the methods includes: identifying a video that comprises images of a human body to be processed; identifying at least one image to be processed, wherein the at least one image is at least one of an optical flow image generated based on a plurality of frames of images in the video, or a composite image of one or more frames of images in the video; performing convolution on the at least one image to obtain a plurality of eigenvectors, wherein the plurality of eigenvectors indicate a plurality of features of different locations in the at least one image; determining a weight coefficient set of each of a plurality of human joints of the human body based on the plurality of eigenvectors, wherein the weight coefficient set comprises a weight coefficient of each of the plurality of eigenvectors for the human joint; weighting the plurality of eigenvectors based on the weight coefficient set to obtain an action feature of each of the plurality of human joints; determining an action feature of the human body based on the action feature of each of the human joints; and
(Continued)

determining an action type of the human body based on the action feature of the human body.

18 Claims, 12 Drawing Sheets

(51) Int. Cl.
*G06N 3/08* (2006.01)
*G06V 10/46* (2022.01)
*G06V 40/10* (2022.01)

(52) U.S. Cl.
CPC .......... *A61B 5/1127* (2013.01); *A61B 5/4528* (2013.01); *G06N 3/08* (2013.01); *G06V 10/469* (2022.01); *G06V 40/10* (2022.01); *G06T 2207/10068* (2013.01)

(58) Field of Classification Search
CPC ............... G06K 9/6247; G06N 3/08; G06T 2207/10068; G06V 10/469; G06V 40/10; G06V 40/20
See application file for complete search history.

(56) References Cited

U.S. PATENT DOCUMENTS

| | | | |
|---|---|---|---|
| 2012/0114226 A1* | 5/2012 | Kameyama | G06V 40/16 382/155 |
| 2013/0250050 A1 | 9/2013 | Kanaujia et al. | |
| 2016/0092726 A1 | 3/2016 | Li et al. | |
| 2017/0169289 A1 | 6/2017 | Li | |

FOREIGN PATENT DOCUMENTS

| | | |
|---|---|---|
| CN | 104899554 A | 9/2015 |
| CN | 105069413 A | 11/2015 |
| CN | 105551182 A | 5/2016 |
| CN | 105787439 A | 7/2016 |
| CN | 105913559 A | 8/2016 |
| CN | 106570480 A | 4/2017 |
| CN | 106682594 A | 5/2017 |
| CN | 107169415 A | 9/2017 |
| CN | 107219925 A | 9/2017 |

OTHER PUBLICATIONS

Michael Edwards et al., "Graph-Based CNN for HAR Graph-Based CNN for Human Action Recognition from 3D Pose," Deep Learning in Irregular Domains Workshop, British Machine Vision Conference, Sep. 7, 2017, 10 pages.

Miao Jie et al., "Temporal Variance Analysis for Action Recognition," IEEE Transactions on Image Processing, vol. 24, No. 12, Dec. 1, 2015, 12 pages.

Cheron et al.,. "P-CNN: Pose-based CNN Features for Action Recognition," International Conference on Computer Vision (ICCV 15), Dec. 2015, 9 pages.

Sharma et al., "Action Recognition Using Visual Attention," International Conference on Learning Representations (ICLR) Workshop, Nov. 2015, 11 pages.

Simonyan et al., "Two-stream convolutional networks for action recognition in videos," arXiv:1406.2199v2 [cs.CV], Nov. 12, 2014, 11 pages.

PCT International Search Report and Written Opinion issued in International Application No. PCT/CN2018/110078 dated Dec. 28, 2018, 15 pages (with English translation).

Office Action issued in Chinese Application No. 201710955087.1 dated Jul. 13, 2022, 6 pages.

Yang et al., "Motion Tracking System by Direct Fusion of RGB-D Camera and Micro-IMU Sensors," Journal of System Simulation, vol. 27, No. 10, Oct. 2015, 7 pages (with English abstract).

* cited by examiner

ACTION RECOGNITION AND POSE ESTIMATION METHOD AND APPARATUS

CROSS-REFERENCE TO RELATED APPLICATIONS

This application is a continuation of International Application No. PCT/CN2018/110078, filed on Oct. 12, 2018, which claims priority to Chinese Patent Application No. 201710955087.1, filed on Oct. 13, 2017. The disclosures of the aforementioned applications are hereby incorporated by reference in their entireties.

TECHNICAL FIELD

This application relates to the field of image processing technologies, and more specifically, to an action recognition and pose estimation method and apparatus.

BACKGROUND

In many scenarios, a human body action in a video needs to be recognized to determine an action type of the human body action. For example, in a surveillance system, to perceive an intention of a person, a human body action in a video obtained by the surveillance system needs to be recognized. In a man-machine interaction system, to understand behavior of a person, a human body action in a video obtained by the man-machine interaction system needs to be recognized.

To recognize the human body action in the video, in an existing solution, some frames of images are extracted from a to-be-processed video, features of the images are extracted by using a convolutional neural network, a confidence level of considering the human body action as each action type is determined based on the features extracted from the images, and an action type of a highest confidence level (higher than a preset threshold) is determined as the action type of the human body in the video.

In the existing solution, features of all regions in the images are extracted. These features include numerous features unrelated to the action. Consequently, a final action recognition effect is unsatisfactory. In addition, in another existing solution, the action is recognized by directly extracting features of some regions in the images. However, an action feature of the human body may not be well reflected by directly and simply extracting the features of some regions in the images, still resulting in relatively low action recognition accuracy.

SUMMARY

This application provides an action recognition and pose estimation method and apparatus, to improve action recognition accuracy.

According to a first aspect, an action recognition method is provided. The method includes: determining a to-be-processed video, where the to-be-processed video is a video that includes images of a human body; determining a to-be-processed image based on the to-be-processed video, where the to-be-processed image is at least one of a first image, or an optical flow image generated based on a plurality of frames of images in the to-be-processed video, where the first image is any frame of image in the to-be-processed video, or the first image is a composite image of a plurality of frames of images in the to-be-processed video; performing convolution on the to-be-processed image to obtain a plurality of eigenvectors, where the plurality of eigenvectors are respectively used to denote features of different locations in the to-be-processed image; determining a weight coefficient set of each human joint of the human body based on the plurality of eigenvectors, where the weight coefficient set of the human joint includes a weight coefficient of each of the plurality of eigenvectors for the human joint, a weight coefficient of a first-type eigenvector is greater than or equal to a weight coefficient of a second-type eigenvector, a distance between a corresponding location of the first-type eigenvector in the to-be-processed image and a corresponding location of the human joint in the to-be-processed image is a first distance, a distance between a corresponding location of the second-type eigenvector in the to-be-processed image and the corresponding location of the human joint in the to-be-processed image is a second distance, the first distance is less than or equal to the second distance, there are a plurality of human joints, and each human joint corresponds to one weight coefficient set; weighting the plurality of eigenvectors based on the weight coefficient set of each human joint to obtain an action feature of each human joint:

determining an action feature of the human body based on the action feature of each human joint; and determining an action type of the human body based on the action feature of the human body.

In this application, the weight coefficient of the first-type eigenvector is greater than or equal to the weight coefficient of the second-type eigenvector, and the distance between the corresponding location of the first-type eigenvector in the to-be-processed image and the corresponding location of the human joint in the to-be-processed image is less than or equal to the distance between the corresponding location of the second-type eigenvector in the to-be-processed image and the corresponding location of the human joint in the to-be-processed image. Therefore, in this application, a weight coefficient of an eigenvector corresponding to a region closer to the human joint is larger. In this way, a feature closely related to an action in the to-be-processed image can occupy a relatively large proportion in action recognition, and a feature less related to the action in the to-be-processed image can occupy a relatively small proportion in the action recognition. In the action recognition according to this application, significance of features of different regions in the to-be-processed image to the action recognition is taken into full account, so that a more robust action feature can be obtained, thereby improving action recognition accuracy.

In a possible implementation, the determining a weight coefficient set of each human joint of the human body based on the plurality of eigenvectors includes: determining the weight coefficient set of each human joint based on the plurality of eigenvectors and cumulative action information of the human body, where the cumulative action information of the human body is used to indicate an action feature of the human body accumulated before a current time point.

In determining the weight coefficient set of each human joint, the cumulative action information of the human body before the current time point is taken into account, so that a larger weight coefficient can be determined for an eigenvector closely related to the action, thereby improving action recognition accuracy. The cumulative action information of the human body before the current time point can be obtained by using, but without limitation, a recurrent neural network. For example, the cumulative action information of the human body before the current time point can be obtained by using a long short term memory (LSTM) module.

In a possible implementation, the determining an action feature of the human body based on the action feature of each human joint includes: weighting or combining action features of all the human joints to obtain the action feature of the human body.

The action features of the human joints are weighted or combined, so that an action feature that is of a human joint and that is relatively closely related to a human body action can occupy a relatively large proportion. In this way, the finally obtained action feature of the human body can better reflect the human body action, thereby improving action recognition accuracy.

In a possible implementation, the determining an action feature of the human body based on the action feature of each human joint includes: weighting or combining action features of all the human joints to obtain action features of human body parts, where the human body includes a plurality of human body parts, and each human body part includes at least one human joint; and weighting or combining the action features of the human body parts to obtain the action feature of the human body.

An action feature of a human body part is obtained based on action features of human joints, and therefore when some joints are obscured, action information can be provided based on action features of the other joints of the human body part, and ultimately an action type of a person can still be recognized when some joints of the human body are obscured.

In a possible implementation, the to-be-processed image includes the first image and the optical flow image, and the performing convolution on the to-be-processed image to obtain a plurality of eigenvectors includes: performing convolution on the first image to obtain a plurality of eigenvectors of the first image: and performing convolution on the optical flow image to obtain a plurality of eigenvectors of the optical flow image; the determining a weight coefficient set of each human joint of the human body based on the plurality of eigenvectors includes: determining a first-type weight coefficient set of each human joint based on the plurality of eigenvectors of the first image; and determining a second-type weight coefficient set of each human joint based on the plurality of eigenvectors of the optical flow image; the weighting the plurality of eigenvectors based on the weight coefficient set of each human joint to obtain an action feature of each human joint includes: weighting the plurality of eigenvectors of the first image based on the first-type weight coefficient set to obtain a first-type action feature of each human joint; and weighting the plurality of eigenvectors of the optical flow image based on the second-type weight coefficient set to obtain a second-type action feature of each human joint; and the determining an action feature of the human body based on the action feature of each human joint includes: weighting or combining first-type action features of all the human joints and second-type action features of all the human joints to obtain the action feature of the human body.

Features are extracted from the first image and the optical flow image that are obtained in the to-be-processed video, and the action is recognized based on the features extracted from the first image and the optical flow image. In this way, both spatial characteristics of the human body action in the to-be-processed video and time change characteristics of the human body action in the to-be-processed video are taken into account, so that action recognition accuracy can be improved.

In a possible implementation, the method further includes: training a neural network, and determining parameters in the neural network, so that a weight coefficient of the first-type eigenvector generated by the neural network is greater than or equal to a weight coefficient of the second-type eigenvector generated by the neural network, where the neural network is used to perform the method according to any one of the first aspect, or the possible implementations of the first aspect.

According to a second aspect, a pose estimation method is provided. The method includes: determining a to-be-processed video, where the to-be-processed video is a video that includes images of a human body; determining a to-be-processed image based on the to-be-processed video, where the to-be-processed image is at least one of a first image, or an optical flow image generated based on a plurality of frames of images in the to-be-processed video, where the first image is any frame of image in the to-be-processed video, or the first image is a composite image of a plurality of frames of images in the to-be-processed video; performing convolution on the to-be-processed image to obtain a plurality of eigenvectors, where the plurality of eigenvectors are respectively used to denote features of different locations in the to-be-processed image; determining a weight coefficient set of each human joint of the human body based on the plurality of eigenvectors, where the weight coefficient set of the human joint includes a weight coefficient of each of the plurality of eigenvectors for the human joint, a weight coefficient of a first-type eigenvector is greater than or equal to a weight coefficient of a second-type eigenvector, a distance between a corresponding location of the first-type eigenvector in the to-be-processed image and a corresponding location of the human joint in the to-be-processed image is a first distance, a distance between a corresponding location of the second-type eigenvector in the to-be-processed image and the corresponding location of the human joint in the to-be-processed image is a second distance, the first distance is less than or equal to the second distance, there are a plurality of human joints, and each human joint corresponds to one weight coefficient set; determining a corresponding region of a first eigenvector of the plurality of eigenvectors in the to-be-processed image as a location of the human joint, where a weight coefficient of the first eigenvector is a first weight coefficient, and the first weight coefficient is a weight coefficient greater than a preset threshold in the weight coefficient set of the human joint; and determining a pose of the human body based on the location of the human joint.

The pose of the human body in the video is estimated based on the weight set of each human joint, so that a feature closely related to an action in the to-be-processed video can occupy a relatively large proportion. Compared with the existing solution in which all features are extracted from an image in a to-be-processed video to estimate a pose, the solution in this application can more accurately determine the pose of the human body in the video.

In a possible implementation, the determining a weight coefficient set of each human joint of the human body based on the plurality of eigenvectors includes: determining the weight coefficient set of each human joint based on the plurality of eigenvectors and cumulative action information of the human body, where the cumulative action information of the human body is used to indicate an action feature of the human body accumulated before a current time point. The cumulative action information of the human body before the current time point can be obtained by using, but without limitation, a recurrent neural network (such as an LSTM module).

In determining the weight coefficient set of each human joint, the cumulative action information of the human body before the current time point is taken into account, so that a larger weight coefficient can be determined for an eigenvector closely related to the action, thereby improving pose estimation accuracy.

In a possible implementation, the to-be-processed image includes the first image and the optical flow image, and the performing convolution on the to-be-processed image to obtain a plurality of eigenvectors includes: performing convolution on the first image to obtain a plurality of eigenvectors of the first image; and performing convolution on the optical flow image to obtain a plurality of eigenvectors of the optical flow image; the determining a weight coefficient set of each human joint of the human body based on the plurality of eigenvectors includes: determining a first-type weight coefficient set of each human joint based on the plurality of eigenvectors of the first image; determining a second-type weight coefficient set of each human joint based on the plurality of eigenvectors of the optical flow image; and determining the weight coefficient set of each human joint based on the first-type weight coefficient set and the second-type weight coefficient set.

Features are extracted from the first image and the optical flow image that are obtained in the to-be-processed video, and the pose is estimated based on the features extracted from the first image and the optical flow image. In this way, both spatial characteristics of the human body action in the to-be-processed video and time change characteristics of the human body action in the to-be-processed video are taken into account, so that pose estimation accuracy can be improved.

In a possible implementation, the determining the weight coefficient set of each human joint based on the first-type weight coefficient set and the second-type weight coefficient set includes: weighting the first-type weight coefficient set and the second-type weight coefficient set to obtain the weight coefficient set of each human joint.

According to a third aspect, an action recognition apparatus is provided. The apparatus includes modules configured to perform the method according to any one of the first aspect, or the possible implementations of the first aspect.

According to a fourth aspect, a pose estimation apparatus is provided. The apparatus includes modules configured to perform the method according to any one of the second aspect, or the possible implementations of the second aspect.

According to a seventh aspect, an action recognition apparatus is provided. The apparatus includes a storage medium and a central processing unit. The storage medium may be a non-volatile storage medium, and the storage medium stores a computer-executable program. The central processing unit is connected to the non-volatile storage medium, and executes the computer-executable program to implement the method according to any one of the first aspect, or the possible implementations of the first aspect.

According to an eighth aspect, a pose estimation apparatus is provided. The apparatus includes a storage medium and a central processing unit. The storage medium may be a non-volatile storage medium, and the storage medium stores a computer-executable program. The central processing unit is connected to the non-volatile storage medium, and executes the computer-executable program to implement the method according to any one of the second aspect, or the possible implementations of the second aspect.

According to a ninth aspect, a chip is provided. The chip includes a processor and a communications interface. The communications interface is configured to communicate with an external device, and the processor is configured to perform the method according to any one of the first aspect, or the possible implementations of the first aspect.

Optionally, in an implementation, the chip may further include a memory. The memory stores an instruction, and the processor is configured to execute the instruction stored in the memory. When the instruction is executed, the processor is configured to perform the method according to any one of the first aspect, or the possible implementations of the first aspect.

According to a tenth aspect, a chip is provided. The chip includes a processor and a communications interface. The communications interface is configured to communicate with an external device, and the processor is configured to perform the method according to any one of the second aspect, or the possible implementations of the second aspect.

Optionally, in an implementation, the chip may further include a memory. The memory stores an instruction, and the processor is configured to execute the instruction stored in the memory. When the instruction is executed, the processor is configured to perform the method according to any one of the second aspect, or the possible implementations of the second aspect.

According to an eleventh aspect, a computer-readable storage medium is provided. The computer-readable storage medium stores program code to be executed by a device. The program code includes an instruction for performing the method according to any one of the first aspect, or the possible implementations of the first aspect.

According to a twelfth aspect, a computer-readable storage medium is provided. The computer-readable storage medium stores program code to be executed by a device. The program code includes an instruction for performing the method according to any one of the second aspect, or the possible implementations of the second aspect.

DESCRIPTION OF EMBODIMENTS

A different region in a video image is of different significance to action recognition, and a region in which a human joint is located is of higher significance to action recognition while a background region is of lower significance. Therefore, to better recognize an action, different image regions may be treated differently in extracting action features of a human body. Specifically, a relatively high weight may be given to an image region closely related to a human joint while a relatively low weight may be given to an image region less related to the human joint. In this way, a human body action in a video can be better recognized, thereby improving action recognition accuracy. An action recognition method in an embodiment of this application is described in detail below with reference to FIG. 1.

Figure 1:
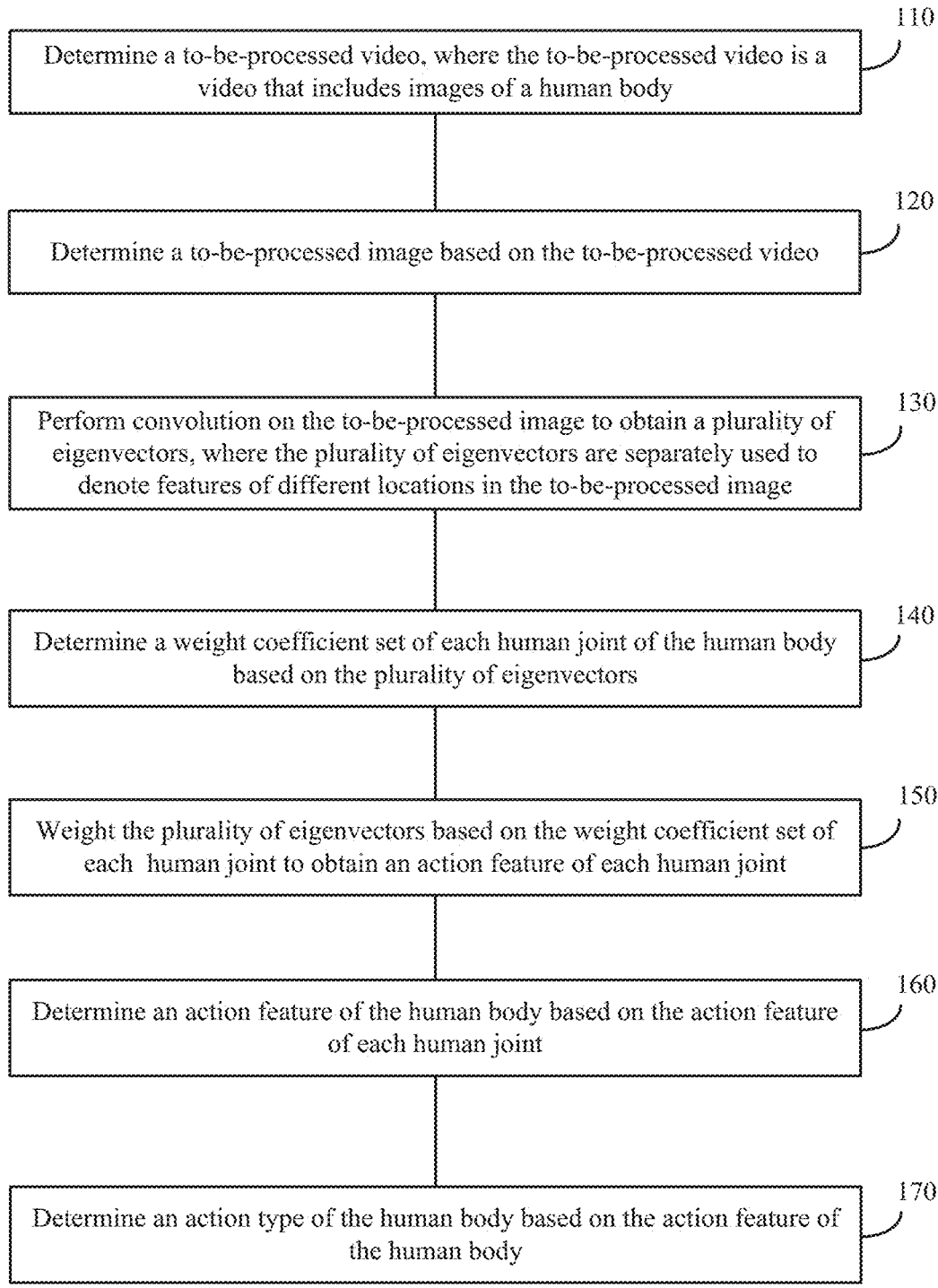
FIG. 1 is a schematic flowchart of an action recognition method according to an embodiment of this application.

FIG. 1 is a schematic flowchart of an action recognition method according to an embodiment of this application. The method shown in FIG. 1 can be applied to a scenario in which a human body action in a video needs to be recognized, such as man-machine interaction, video surveillance, assisted driving, and autonomous driving. In addition, the method shown in FIG. 1 may be performed by a machine in a man-machine interaction system, a video surveillance system, an assisted driving system, or an autonomous driving system.

The method shown in FIG. 1 includes steps 110 to 170. Steps 110 to 170 are separately described below.

110. Determine a to-be-processed video, where the to-be-processed video is a video that includes images of a human body.

It should be understood that, the to-be-processed video may be a video that includes human body-related images. For example, the to-be-processed video may be any one of: a video that includes human body-related images and that is obtained through surveillance by a video surveillance system; a video that includes passerby-related images and that is obtained by an assisted driving system or an autonomous driving system; or a man-machine interaction video captured by a man-machine interaction system.

120. Determine a to-be-processed image based on the to-be-processed video.

The to-be-processed image may be at least one of:
a first image; or
an optical flow image.

The first image is any frame of image in the to-be-processed video, or the first image is a composite image of a plurality of frames of images in the to-be-processed video. The optical flow image is an image generated based on a plurality of frames of images in the to-be-processed video.

130. Perform convolution on the to-be-processed image to obtain a plurality of eigenvectors, where the plurality of eigenvectors are used to denote features of different locations in the to-be-processed image.

In step 130, the performing convolution on the to-be-processed image may specifically include the following three cases:

Case 1: Performing convolution on the first image to obtain a plurality of eigenvectors of the first image;

Case 2: Performing convolution on the optical flow image to obtain a plurality of eigenvectors of the optical flow image; and Case 3: Performing convolution on the first image and the optical flow image to obtain a plurality of eigenvectors of the first image and a plurality of eigenvectors of the optical flow image.

It should be understood that, in obtaining an optical flow image, a plurality of frames of images or pictures may be extracted from the to-be-processed video first, and then an optical flow image of the to-be-processed video is generated based on the plurality of extracted frames of images.

For example, several frames of images $I_t, I_{t-1} \ldots I_{t-N}$ are obtained from the to-be-processed video, where $I_t$ is a frame of image corresponding to a current time point t, and $I_{t-1}$ is a frame of image corresponding to a time point t−1 before the current time point t. Optical flows of the images in an x direction and a y direction may be calculated to obtain an optical flow image that has 2N (N is an integer greater than 1) channels.

In step 130, a convolution operation may be performed on the to-be-processed video by using a convolutional neural network, to obtain a convolution feature map and then obtain a plurality of eigenvectors.

Figure 2:
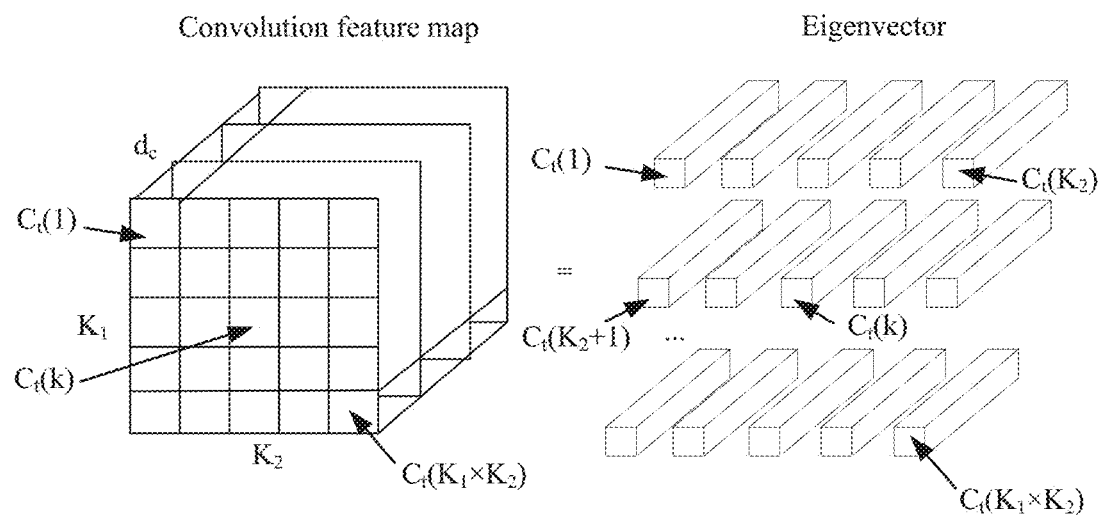
FIG. 2 is a schematic diagram of a convolution feature map and an eigenvector.

Specifically, as shown in FIG. 2, convolution may be performed on the to-be-processed video to obtain a convolution feature map (convolution feature map) $C_t$, where $C_t$ has $d_c$ channels, and a resolution of each channel is $K_1 \times K_2$, and therefore the convolution feature map may be denoted by a $K_1 \times K_2 \times d_c$ matrix, that is, $C_t \in R^{K_1 \times K_2 \times d_c}$.

Each channel of the convolution feature map has $K_1 \times K_2$ elements, and the $k^{th}$ element (k=1, 2, . . . , $K_1 \times K_2$) on each channel forms the $k^{th}$ eigenvector $C_t(k)$ of the convolution feature map. Therefore, the convolution feature map may also be denoted by $K_1 \times K_2$ eigenvectors. A dimension of each vector is $d_c \times 1$, that is, $C_t(k) \in R^{d_c}$, k=1, . . . , $K_1 \times K_2$, as shown in FIG. 2.

If an input image is divided into $K_1 \times K_2$ regions, the $k^{th}$ eigenvector $C_t(k)$ corresponds to a feature of the $k^{th}$ region (or location) in the image.

140. Determine a weight coefficient set of each human joint of the human body based on the plurality of eigenvectors.

It should be understood that, in step 140, there are a plurality of human joints, and the weight coefficient set of each human joint needs to be determined based on the plurality of eigenvectors. In other words, each human joint has one weight coefficient set.

In addition, in step 140, the weight coefficient set of the human joint includes a weight coefficient of each of the plurality of eigenvectors for the human joint. In addition, a weight coefficient of a first-type eigenvector of the plurality of eigenvectors is greater than or equal to a weight coefficient of a second-type eigenvector of the plurality of eigenvectors. A distance between a corresponding location of the first-type eigenvector in the to-be-processed image and a corresponding location of the human joint in the to-be-processed image is a first distance, a distance between a corresponding location of the second-type eigenvector in the to-be-processed image and a corresponding location of the human joint in the to-be-processed image is a second distance, and the first distance is less than or equal to the second distance.

Figure 3:
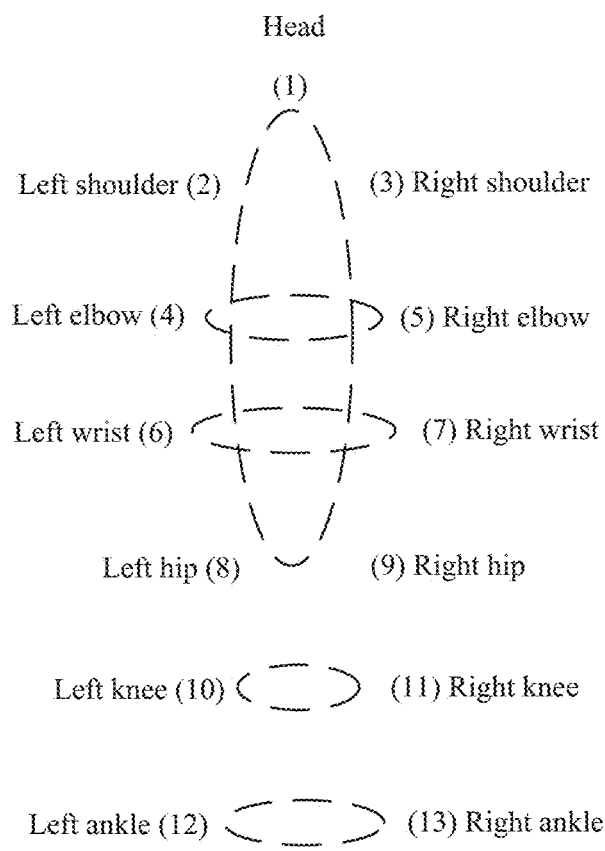
FIG. 3 is a schematic diagram of human joints.

As shown in FIG. 3, a head (head), a left shoulder (shoulder), a right shoulder, a left elbow (elbow), a right elbow, a left wrist (wrist), a right wrist, a left hip (hip), a right hip, a left knee (knee), a right knee, a left ankle (ankle), and a right ankle are all human joints. To be specific, FIG. 3 shows 13 human joints, and these human joints are numbered (1) to (13). It should be understood that, the human joints in this application are not limited to the foregoing joints.

150. Weight the plurality of eigenvectors based on the weight coefficient set of each human joint to obtain an action feature of each human joint.

Specifically, a product of each of the plurality of eigenvectors and the corresponding weight coefficient may be determined, and then a plurality of obtained products are summed up, and a result of the summation is determined as the action feature of the human joint. For example, the action feature of each human joint may be determined by using a formula (2). In the formula (2). $F_t^J$ is an action feature of a human joint J, $C_t(k)$ is an eigenvector, and $\alpha_t^J(k)$ is a weight coefficient of $C_t(k)$.

$$F_t^J = \Sigma_k \alpha_t^J(k) \cdot C_t(k) \qquad (2)$$

160. Determine an action feature of the human body based on the action feature of each human joint.

It should be understood that, in step 160, the finally determined action feature of the human body may be an eigenvector (the eigenvector may be a 1*N vector), and the eigenvector includes action information of the human body.

The action feature of the human body may be specifically determined based on action features of the plurality of human joints in the following two manners.

Manner 1: Weighting or combining the action features of the human joints to obtain the action feature of the human body.

It should be understood that, because there are the plurality of human joints, the weighting or combining the action features of the human joints factually means weighting or combining the action features of the plurality of human joints to obtain the action feature of the human body.

Because an action feature can be denoted by an eigenvector, combining the action features of the human joints to obtain the action feature of the human body may be specifically connecting eigenvectors corresponding to the action features of all the human joints together to form a new eigenvector. The new eigenvector is used to denote the action feature of the human body. For example, if there are L (L is an integer greater than 1) human joints, and an eigenvector corresponding to the action feature of each human joint is a 1×M (M is an integer greater than 1) eigenvector. L 1×M eigenvectors may be combined to obtain a 1×N eigenvector, where N=L×M.

In weighting the action features of the plurality of human joints, weight coefficients for action features of different human joints may be the same or different.

When the weight coefficients for the action features of the different human joints are the same, the weighting is equivalent to directly adding up the action features of the different human joints to obtain the action feature of the human body.

When the weight coefficients for the action features of the different human joints are different, a weight coefficient for an action feature of a human joint may be determined based on significance of the human joint to action recognition. For example, a weight coefficient for an action feature of a human joint of higher significance to the action recognition is larger, and a weight coefficient for an action feature of a human joint of lower significance to the action recognition is smaller.

Significance or a significance level of a human joint to action recognition may be preset based on an application scenario of the action recognition. For example, in a video of baseball sports, significance of a left wrist or a right wrist to action recognition is higher than significance of a head to the action recognition. Therefore, a weight coefficient for an action feature of the left wrist or the right wrist is larger than a weight coefficient for an action feature of the head. In addition, a weight coefficient for each human joint may be trained based on a neural network, to enable a weight coefficient for an action feature of a human joint of higher significance to action recognition to be larger than a weight coefficient for an action feature of a human joint of lower significance to the action recognition process.

In this application, the action features of the human joints are weighted or combined, so that an action feature that is of a human joint and that is relatively closely related to a human body action can occupy a relatively large proportion. In this way, the finally obtained action feature of the human body can better reflect the human body action, thereby improving action recognition accuracy.

Manner 2: Determining action features of human body parts of the human body based on the action features of the human joints; and determining the action feature of the human body based on the action features of the human body parts.

The human body includes a plurality of human body parts, and each human body part includes at least one human joint.

Specifically, in recognizing a human body action in a video, the human body may further be divided into different human body parts. Each human body part may include one or more human joints. Further, a human body part may include human joints that are in a specific semantic relationship. For example, the human body may be divided into five human body parts: a torso, elbows, wrists, knees, and ankles. The torso includes a head, a left shoulder, a right shoulder, a left hip, and a right hip; the elbows include a left elbow and a right elbow; the wrists include a left wrist and a right wrist; the knees include a left knee and a right knee; and the ankles include a left ankle and a right ankle.

When the human body is divided into the five human body parts that are the torso, the elbows, the wrists, the knees, and the ankles, a correspondence between the five human body parts and the human joints shown in FIG. 3 is shown in Table 1.

TABLE 1

Correspondence between the human body parts and the human joints

| Human body part | Human joint |
| --- | --- |
| Torso | (1), (2), (3), (8), (9) |
| Elbows | (4), (5) |

TABLE 1-continued

Correspondence between the human body parts and the human joints

| Human body part | Human joint |
| --- | --- |
| Wrists | (6), (7) |
| Knees | (10), (11) |
| Ankles | (12), (13) |

It should be understood that, each human body part includes at least one human joint, and therefore in determining the action features of the human body parts based on the action features of the human joints in manner 2, action features of all human joints that form a human body part may be specifically weighted or combined to obtain an action feature of the human body part. Weight coefficients for the human joints that form the human body part may be the same or different.

Specifically, an action feature of each human body part may be determined by using a formula (3).

$$F_t^P = \Sigma_{J \in P} \Sigma_k \alpha_t^J(k) \cdot C_t(k) \quad (3)$$

In the formula (3), P denotes a human body part, J denotes a human joint that forms the human body part P, $C_t(k)$ denotes an eigenvector of a location k in the to-be-processed image, and $\alpha_t^J(k)$ denotes a weight coefficient of $C_t(k)$ for the human joint J. It should be understood that, in the formula (3), action features of all human joints that form the human body part P are added up to obtain an action feature of the human body part P. To be specific, weight coefficients for the action features of all the joints in the human body part P are the same.

Optionally, in manner 2, the determining the action feature of the human body based on the action features of the human body parts specifically includes: weighting or combining the action features of the human body parts to obtain the action feature of the human body.

It should be understood that, there are the plurality of human body parts, and therefore the weighting or combining the action features of the human body parts to obtain the action feature of the human body factually means weighting or combining the action features of the plurality of human body parts to obtain the action feature of the human body.

In addition, in weighting the action features of the plurality of human body parts, weight coefficients for action features of different human body parts may be the same or different.

When the weight coefficients for the action features of the different human body parts are different, a weight coefficient for an action feature of a human body part may be determined based on significance of the human body part to the action recognition. A weight coefficient for an action feature of a human body part of higher significance to the action recognition is larger, and a weight coefficient for an action feature of a human body part of lower significance to the action recognition is smaller. For example, the torso is of higher significance to the action recognition than the ankles, and therefore a weight coefficient for an action feature of the torso is larger than a weight coefficient for an action feature of the ankles.

Specifically, in manner 2, the action feature of the human body can be obtained by using a formula (4).

$$S_t = \text{PartPool}(F_t^{P1}, F_t^{P2}, \ldots, F_t^{PX}) \quad (4)$$

In the formula (4), $P_1$ to $P_X$ denote human body parts, there are X (X is an integer greater than 1) human body parts, $F_t^{P1}, F_t^{P2}, \ldots, F_t^{PX}$ are eigenvectors of all the human body parts and are used to denote action features of all the human body parts, and $S_t$ is a finally obtained eigenvector of the human body and is used to denote the action feature of the human body.

$S_t$ may be determined by using a PartPool function in (but without limitation) the following manners.

(1) Select a maximum value of each component in $F_t^{P1}$, $F_t^{P2}, \ldots, F_t^{PX}$ as a value of a corresponding component in $S_t$.

(2) Use an average of each component in $F_t^{P1}, F_t^{P2}, \ldots, F_t^{PX}$ as a value of a corresponding component in $S_t$.

(3) Directly use, as $S_t$, a one-dimensional vector obtained by combining $F_t^{P1}, F_t^{P2}, \ldots, F_t^{PX}$.

In this application, an action feature of a human body part is obtained based on action features of human joints, and therefore when some joints are obscured, action information can be provided based on action features of the other joints of the human body part, and ultimately an action type of a person can still be recognized when some joints of the human body are obscured.

170. Determine an action type of the human body based on the action feature of the human body.

Optionally, the determining an action type of the human body based on the action feature of the human body specifically includes: determining, based on the action feature of the human body, a confidence level of considering a human body action as each action type; and determining the action type of the human body based on the confidence level of considering the human body action as each action type.

It should be understood that, action types of the human body may be preset. For example, the action types of the human body in this application may specifically include: run (run), walk (walk), baseball_pitch (baseball_pitch), baseball_swing (baseball_swing), bowl (bowl), clean_and_jerk (clean_and_jerk), golf_swing (golf_swing), jump_rope (jump_rope), pullup (pullup), pushup (pushup), situp (situp), squat (squat), strum_guitar (strum_guitar), tennis_serve (tennis_serve), tennis_forehand (tennis_forehand), and the like. It should be understood that, herein shows merely specific examples of action types, and the action types included in the embodiments of this application are not limited thereto.

In addition, in this application, all action types may be preset based on an application scenario of action recognition. For example, when the action recognition method in this embodiment of this application is applied to a scenario of an assisted driving system or an autonomous driving system, the preset action types of the human body may include walk, run, watch a mobile phone, and the like.

In addition, after the confidence level of considering the human body action as each action type is determined, an action type of a highest confidence level (higher than a preset threshold) may be determined as the action type of the human body. For example, if it is determined that confidence levels of considering the human body action as run, walk, and watch a mobile phone are 0.8, 0.6, and 0.3 respectively, and a confidence level threshold is 0.5, it can be determined that the action type of the human body is run.

In this application, the action feature of the human body is determined based on weight sets of the human joints and the plurality of eigenvectors, so that a feature closely related to the action in the to-be-processed video can occupy a relatively large proportion. Compared with the existing solution in which these features are treated equally, the solution in this application can improve action recognition accuracy.

Optionally, in an embodiment, the determining a weight coefficient set of each human joint of the human body based on the plurality of eigenvectors in step 140 specifically includes: determining the weight coefficient set of each human joint based on the plurality of eigenvectors and cumulative action information of the human body, where the cumulative action information of the human body is used to indicate an action feature of the human body accumulated before a current time point. The cumulative action information of the human body before the current time point can be obtained by using, but without limitation, a recurrent neural network (such as an LSTM module).

In this application, in determining the weight coefficient set of each human joint, the cumulative action information of the human body before the current time point is taken into account, so that a larger weight coefficient can be determined for an eigenvector closely related to the action, thereby improving action recognition accuracy.

It should be understood that, the determining the weight coefficient set of each human joint may be determining a weight coefficient of each of the plurality of eigenvectors for the human joint.

Specifically, the weight coefficient of each eigenvector for the human joint may be determined by using a formula (5).

$$\tilde{\alpha}_t^J(k) = v^J \tan h(A_h^P h_{t-1} + A_c^P C_t(k) + b^P) \qquad (5)$$

In the formula (5), $C_t(k)$ is an eigenvector in a location k of the to-be-processed video, J is a human joint, P is a human body part that includes the human joint J, $v^J$ is a parameter specific to the human joint J, $\{A_h^P, A_c^P, b^P\}$ is parameters that are common to all human joints in the human body part P, $\tilde{\alpha}_t^J(k)$ is a weight coefficient of the eigenvector $C_t(k)$ for the human joint J, P is a human body part that includes J, and $\tilde{\alpha}_t^J(k)$ is a weight coefficient of $C_t(k)$ for the human joint J. The parameters $v^J$, $A_h^P$, $A_c^P$, $b^P$ are obtained by training a neural network that performs the action recognition method in this embodiment of this application.

Further, $\tilde{\alpha}_t^J(k)$ may be normalized by using a formula (6) to obtain a normalized weight coefficient.

$$\alpha_t^J(k) = \frac{\exp\{\tilde{\alpha}_t^J(k)\}}{\sum_k \exp\{\tilde{\alpha}_t^J(k)\}} \qquad (6)$$

In the formula (6), $\tilde{\alpha}_t^J(k)$ is an unnormalized weight coefficient of $C_t(k)$ for the human joint J, $\alpha_t^J(k)$ is a weight coefficient obtained by normalizing $\tilde{\alpha}_t^J(k)$, and $\alpha_t^J(k)$ can represent significance of the eigenvector $C_t(k)$ in the location k of the to-be-processed video to the action recognition. A larger value of $\alpha_t^J(k)$ indicates higher significance of $C_t(k)$ to the action recognition. $\alpha_t^J(k)$ may also denote a probability of existence of a corresponding human joint in the location k of the to-be-processed video. A larger value of $\alpha_t^J(k)$ indicates a higher probability of existence of the human joint in this location.

Figure 4:
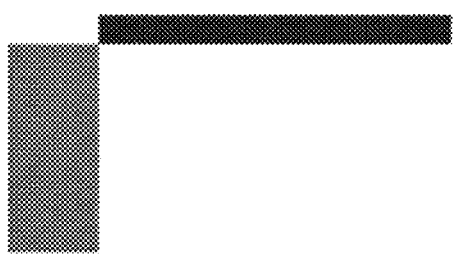
FIG. 4 is a schematic diagram of values of weight coefficients in a weight coefficient set of a left ankle of a human body.
Figure 5:
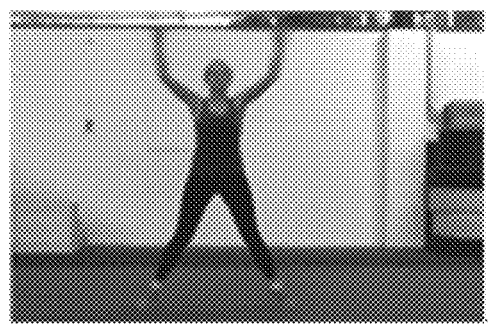
FIG. 5 is a human body image.
Figure 6:
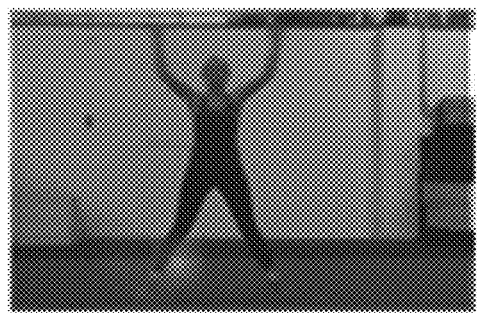
FIG. 6 is a schematic diagram of superimposing a schematic diagram of values of weight coefficients in a weight coefficient set onto a human body image.

FIG. 4 shows values of weight coefficients in a weight coefficient set of a left ankle. In FIG. 4, a weight coefficient in a brighter region is larger. The lower left region in FIG. 4 is obviously brighter than the other regions in FIG. 4. That is because this region is around the left ankle. For this reason, the weight coefficient in this region is relatively large. To conveniently display the weight coefficient set of the human joint, a value map of weight coefficients in the weight coefficient set of the human joint is generally superimposed onto an image extracted from the to-be-processed video. Specifically. FIG. 4 is superimposed onto FIG. 5 to obtain FIG. 6. As shown in FIG. 6, a region around the left ankle of the human body is obviously brighter than the other regions.

When the to-be-processed image in step 120 includes the first image and the optical flow image, the processing in steps 130 to 160 is specifically as follows:

In step 130, the performing convolution on the to-be-processed image to obtain a plurality of eigenvectors includes: performing convolution on the first image to obtain a plurality of eigenvectors of the first image; and performing convolution on the optical flow image to obtain a plurality of eigenvectors of the optical flow image.

In step 140, the determining a weight coefficient set of each human joint of the human body based on the plurality of eigenvectors includes: determining a first-type weight coefficient set of each human joint based on the plurality of eigenvectors of the first image; and determining a second-type weight coefficient set of each human joint based on the plurality of eigenvectors of the optical flow image.

In step 150, the weighting the plurality of eigenvectors based on the weight coefficient set of each human joint to obtain an action feature of the human joint includes: weighting the plurality of eigenvectors of the first image based on the first-type weight coefficient set to obtain a first-type action feature of each human joint; and weighting the plurality of eigenvectors of the optical flow image based on the second-type weight coefficient set to obtain a second-type action feature of each human joint.

In step 160, the determining an action feature of the human body based on the action feature of each human joint includes: weighting or combining first-type action features of all the human joints and second-type action features of all the human joints to obtain the action feature of the human body.

In this embodiment of this application, features are extracted from the first image and the optical flow image that are obtained in the to-be-processed video, and the action is recognized based on the features extracted from the first image and the optical flow image. In this way, both spatial characteristics of the human body action in the to-be-processed video and time change characteristics of the human body action in the to-be-processed video are taken into account, so that action recognition accuracy can be improved.

Optionally, in determining the action type of the human body based on the action feature of the human body, an action feature of the human body may be determined based on each of the first image and the optical flow image, and then a first-type confidence level of considering the human body action as each action type is determined based on an action feature of the human body that is obtained based on the first image, and a second-type confidence level of considering the human body action as each action type is determined based on an action feature of the human body that is obtained based on the optical flow image. Subsequently, the first-type confidence level and the second-type confidence level are weighted to obtain the confidence level of considering the human body action as each action type. Finally, the action type of the human body is determined based on the confidence level of considering the human body action as each action type.

It should be understood that, herein, the first-type confidence level is a confidence level that is of considering the human body action as each action type and that is determined based on the action feature of the to-be-processed image, and the second-type confidence level is a confidence level that is of considering the human body as each action type and that is determined based on the optical flow image in the to-be-processed video.

The first-type confidence level and the second-type confidence level are jointly taken into account, so that the action type of the human body in the video can be more accurately recognized.

In weighting the first-type confidence level and the second-type confidence level, a weight coefficient of the first-type confidence level may be the same as that of the second-type confidence level. In this case, the weighting the first-type confidence level and the second-type confidence level is equivalent to averaging the first-type confidence level and the second-type confidence level.

Optionally, in an embodiment, before determining the weight coefficient set of each human joint based on the plurality of eigenvectors, the method shown in FIG. 1 further includes: training a neural network that performs the method shown in FIG. 1, and determining parameters in the neural network (the parameters may be some parameters of the neural network, or the parameters are some parameters of a model constituted by the neural network), so that a weight coefficient of the first-type eigenvector generated by the neural network is greater than or equal to a weight coefficient of the second-type eigenvector generated by the neural network.

Specifically, the action recognition method in this embodiment of this application may be implemented by a neural network. To be specific, the to-be-processed video is input into the neural network, and the neural network recognizes the human body action in the to-be-processed video. Before the action recognition, the neural network needs to be trained. In this embodiment of this application, the training of the neural network can be surveilled by using action types of a human body in a training video and a pose of the human body in each frame of image in the video, errors of action recognition and pose estimation are jointly taken into account, so that a total error of the action recognition and the pose estimation is less than a specific threshold.

In training the neural network, a total loss of action recognition and pose estimation may satisfy a formula (7).

$$L_{total} = \lambda_{action} L_{action} + \lambda_{pose} L_{pose} + \lambda_\Theta \|\Theta\|^2 \quad (7)$$

In the formula (7), $L_{action}$ denotes an action recognition loss, $L_{pose}$ denotes a pose estimation loss, $\|\Theta\|^2$ is a regularization term and denotes a square of a modulus of all parameters that need to be learned in the network, and $\lambda_{action}$, $\lambda_{pose}$, and $\lambda_\Theta$ are weight coefficients of these three terms respectively.

$L_{action}$ satisfies a formula (8).

$$L_{action} = \Sigma_{t=1}^T \Sigma_{c=1}^C y_{t,c} \log \hat{y}_{t,c} \quad (8)$$

In the formula (8), $y_t$ is a true value of action recognition, $\hat{y}_t$ is a predicted value of action recognition. T is a quantity of frames in the training video, and C is a quantity of action types.

For $L_{pose}$, a true value $M_t^J(k)$ of a weight coefficient set of each frame of image in the training video for different human joints is generated first based on a true value of a human body pose in training data, and then a distance between $\alpha_t^J(k)$ and $M_t^J(k)$ is used as a loss, that is, $L_{pose}$.

$$L_{pose} = \Sigma_J \Sigma_{t=1}^T \Sigma_{k=1}^{K^{K_1 \times K_2}} (M_t^J(k) - \alpha_t^J(k)) \quad (9)$$

The errors of action recognition and pose estimation are jointly taken into account in a training process, so that the trained neural network can achieve a better effect when performing action recognition.

An action recognition method in an embodiment of this application is described in detail below with reference to FIG. 7.

701. Obtain a to-be-processed video.

Specifically, a video may be obtained from a video surveillance system, a man-machine interaction system, an assisted driving system, or the like. It should be understood that, the video is a video that includes a human body, and an action type of the human body in the video needs to be recognized.

702. Extract an image from the video.

Specifically, in step 702, an image $I_t$ at a current time point t may be extracted from the video directly.

703. Perform convolution on the image.

In step 703, a convolutional neural network may be used to perform convolution on the image $I_t$ extracted in step 702, to obtain a convolution feature map, and then a plurality of eigenvectors are obtained based on the convolution feature map.

704. Determine a weight coefficient set of each human joint.

The determining a weight coefficient set of each human joint specifically includes: based on the plurality of eigenvectors $C_t(k)$ obtained in step 703 and a state vector $h_{t-1}$ that is of the image $I_t$ and that is obtained at a previous time point, determining a weight coefficient $\alpha_t^J(k)$ of each of the plurality of eigenvectors for the human joint. A specific calculation process is described below.

An unnormalized weight coefficient $\tilde{\alpha}_t^J(k)$ is determined first by using a formula (10), and then by using a formula (11), $\tilde{\alpha}_t^J(k)$ is normalized to obtain $\alpha_t^J(k)$.

$$\tilde{\alpha}_t^J(k) = v^J \tanh(A_h^P h_{t-1} + A_c^P C_t(k) + b^P) \quad (10)$$

$$\alpha_t^J(k) = \frac{\exp\{\tilde{\alpha}_t^J(k)\}}{\sum_k \exp\{\tilde{\alpha}_t^J(k)\}} \quad (11)$$

In the formula (10), J denotes a different human joint, and P denotes a different human body part. Different human joints in a same human body part share same parameters $\{A_h^P, A_c^P, b^P\}$. In addition, each human joint has its own parameter $v^J$. In this way $\tilde{\alpha}_t^J(k)$ not only represents a feature of the human joint J, but also integrates information about a human body part that includes the human joint J.

For a better understanding of the formula (10), values of the parameters and variables are described below with examples. For example, $v^J$ is a 1×32 vector, $A_h^P$ is a 3×512 vector, $h_{t-1}$ is a 512×1 vector, $A_c^P$ is a 32×1024 vector, $C_t(k)$ is a 1024×1 vector, and $b^P$ is a 32×1 vector. In this case, $\tilde{\alpha}_t^J(k)$ obtained by using the formula (10) is a specific value.

705. Generate action features of human body parts.

In step 705, the action features of the human body parts may be specifically determined based on the plurality of eigenvectors determined in step 703 and the weight coefficient set of each human joint determined in step 704.

Specifically, the weight coefficient $\alpha_t^J(k)$ is applicable to $C_t(k)$ in different locations k, and then action features of all human joints in the same human body part are added up to obtain an action feature $F_t^P$ of the human body part, as shown in a formula (12):

$$F_t^P = \Sigma_{J \in P} \Sigma_k \alpha_t^J(k) C_t(k) \quad (12)$$

$F_t^P$ can represent a feature related to a human body part P in a complex action.

706. Generate an action feature of the human body.

Specifically, in generating the action feature of the human body, the action features of the different human body parts obtained in step 705 may be combined to generate the action feature $S_t$ of the human body.

707. Update an action feature of the human body accumulated before the current time point.

$S_t$ generated in step 706 is used as an input, to update the action feature $h_{t-1}$ of the human body accumulated at the previous time point to $h_t$. The update of the cumulative action feature of the human body may be implemented by a long short term memory (LSTM) module. The LSTM module may be a type of recurrent neural network, and may be in diversified forms. The LSTM module used herein may be a basic LSTM module or a variant of the LSTM module.

708. Recognize an action of the human body in the video.

Specifically, the cumulative action feature $h_t$ of the human body finally obtained in step 707 is input into an action recognition module to recognize the action type. Specifically, a confidence level of considering $h_t$ as each action type may be calculated by using a formula (13).

$$\hat{y}_t = \text{softmax}(U_y^h h_t + b_y) \quad (13)$$

In the formula (13), $\hat{y}_t$ is a confidence level of considering the human body action as a specific action type, and $U_y^h$ and $b_y$ are parameters corresponding to the action type. After the confidence level of considering the human body action as each action type is determined by using the formula (13), an action type of a highest confidence level may be determined as the action type of the human body.

It should be understood that, after step 701 of the foregoing method, several frames of images may further be extracted from the to-be-processed video, and then an optical flow image of the to-be-processed video is generated based on the several frames of images. Subsequently, processing on the optical flow image is exactly the same as the processing in steps 703 to 708. In addition, after a confidence level of considering the human body action as each action type is obtained based on the optical flow image and with reference to the formula (13), a confidence level calculated from the image and a confidence level calculated from the optical flow image that correspond to each action type may be averaged, and then an action type of a highest confidence level is selected as the action type of the human body.

In addition to recognizing the action type of the human body in the video, this application further provides a pose estimation method that is used to estimate a pose of the human body in the video. The pose estimation may be recognizing a human joint in a to-be-processed image, and determining a location of the human joint in the to-be-processed image.

Figure 8:
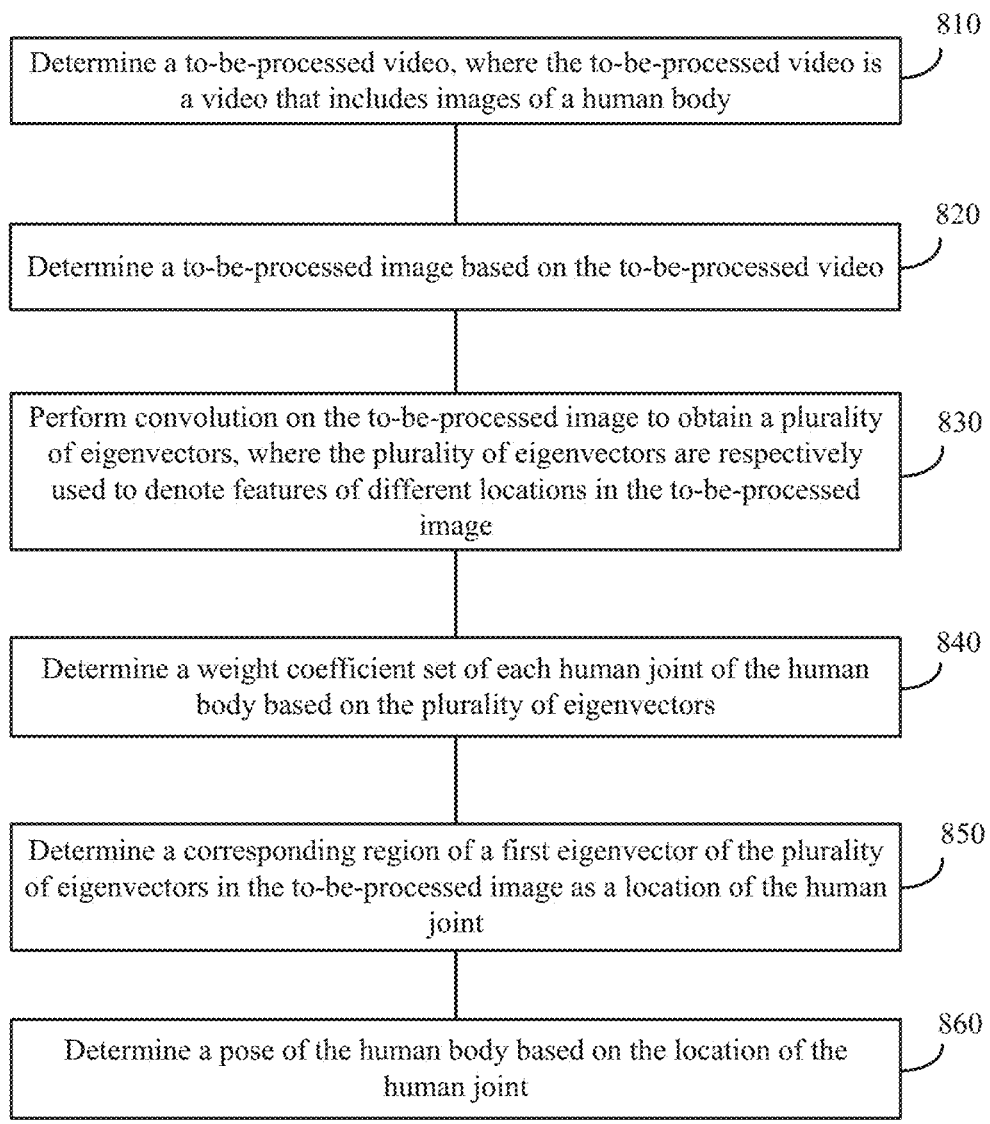
FIG. 8 is a schematic flowchart of a pose estimation method according to an embodiment of this application.

FIG. 8 shows a pose estimation method according to an embodiment of this application. Similar to the action recognition method shown in FIG. 1, the pose estimation method shown in FIG. 8 can also be applied to a scenario in which a human body action in a video needs to be recognized, such as man-machine interaction, video surveillance, assisted driving, and autonomous driving. In addition, the pose estimation method shown in FIG. 8 may be performed by a machine in a man-machine interaction system, a video surveillance system, an assisted driving system, or an autonomous driving system.

The method shown in FIG. 8 includes steps 810 to 860. Steps 810 to 860 are described below.

810. Determine a to-be-processed video, where the to-be-processed video is a video that includes images of a human body.

The to-be-processed video in step 810 may be a video that includes human body-related images. For example, the to-be-processed video may be any one of: a video that includes human body-related images and that is obtained through surveillance by a video surveillance system; a video that includes passerby-related images and that is obtained by an assisted driving system or an autonomous driving system; or a man-machine interaction video captured by a man-machine interaction system.

820. Determine a to-be-processed image based on the to-be-processed video.

The to-be-processed image may be at least one of:

a first image; or an optical flow image.

The first image is a frame of image in the to-be-processed video, or the first image is a composite image of a plurality of frames of images in the to-be-processed video. The optical flow image is an image generated based on a plurality of frames of images in the to-be-processed video.

830. Perform convolution on the to-be-processed image to obtain a plurality of eigenvectors, where the plurality of eigenvectors are respectively used to denote features of different locations in the to-be-processed image.

Similar to the method shown in FIG. 1, the convolution performed on the to-be-processed video in step 830 may also specifically include three cases:

Case 4: Performing convolution on the first image to obtain a plurality of eigenvectors of the first image;

Case 5: Performing convolution on the optical flow image to obtain a plurality of eigenvectors of the optical flow image; and Case 6: Performing convolution on the first image and the optical flow image to obtain a plurality of eigenvectors of the first image and a plurality of eigenvectors of the optical flow image.

It should be understood that, in obtaining an optical flow image, a plurality of frames of images may be extracted from the to-be-processed video first, and then an optical flow image of the to-be-processed video is generated based on the plurality of extracted frames of images.

840. Determine a weight coefficient set of each human joint of the human body based on the plurality of eigenvectors.

It should be understood that, in step 840, there are a plurality of human joints, and the weight coefficient set of each human joint needs to be determined based on the plurality of eigenvectors. In other words, each human joint has one weight coefficient set.

In addition, in step 840, the weight coefficient set of the human joint includes a weight coefficient of each of the plurality of eigenvectors for the human joint. In addition, a weight coefficient of a first-type eigenvector of the plurality of eigenvectors is greater than or equal to a weight coefficient of a second-type eigenvector of the plurality of eigenvectors. A distance between a corresponding location of the first-type eigenvector in the to-be-processed image and a corresponding location of the human joint in the to-be-processed image is a first distance, a distance between a corresponding location of the second-type eigenvector in the to-be-processed image and a corresponding location of the human joint in the to-be-processed image is a second distance, and the first distance is less than or equal to the second distance.

Optionally, in an embodiment, the determining a weight coefficient set of each human joint of the human body based on the plurality of eigenvectors in step 840 specifically includes: determining the weight coefficient set of each human joint based on the plurality of eigenvectors and cumulative action information of the human body, where the cumulative action information of the human body is used to indicate an action feature of the human body accumulated before a current time point.

In determining the weight coefficient set of each human joint, the cumulative action information of the human body before the current time point is taken into account, so that a larger weight coefficient can be determined for an eigenvector closely related to the action, thereby improving pose estimation accuracy.

It should be understood that, the determining the weight coefficient set of each human joint may be determining a weight coefficient of each of the plurality of eigenvectors for the human joint.

Specifically, the weight coefficient of each eigenvector for the human joint may be determined by using the foregoing formula (5) and formula (6).

850. Determine a corresponding region of a first eigenvector of the plurality of eigenvectors in the to-be-processed image as a location of the human joint.

In step 850, a weight coefficient of the first eigenvector is a first weight coefficient, and the first weight coefficient is a weight coefficient greater than a preset threshold in the weight coefficient set of the human joint.

It should be understood that, in step 850, the first weight coefficient may alternatively be a largest weight coefficient in the weight coefficient set of the human joint (the human joint herein may be any human joint of the human body, for example, a head or a left ankle).

860. Determine a pose of the human body based on the location of the human joint.

In step 860, the location of the human joint may be marked, and all the human joints may be connected. In this way, the pose of the human body is determined.

In this application, the pose of the human body in the video is estimated based on the weight set of each human joint, so that a feature closely related to an action in the to-be-processed video can occupy a relatively large proportion. Compared with the existing solution in which all features are extracted from an image in a to-be-processed video to estimate a pose, the solution in this application can more accurately determine the pose of the human body in the video.

When the to-be-processed image in step 820 includes the first image and the optical flow image, the processing in steps 830 and 840 is specifically as follows:

In step 830, the performing convolution on the to-be-processed image to obtain a plurality of eigenvectors includes: performing convolution on the first image to obtain a plurality of eigenvectors of the first image; and performing convolution on the optical flow image to obtain a plurality of eigenvectors of the optical flow image.

In step 840, the determining a weight coefficient set of each human joint of the human body based on the plurality of eigenvectors includes: determining a first-type weight coefficient set of each human joint based on the plurality of eigenvectors of the first image; determining a second-type weight coefficient set of each human joint based on the plurality of eigenvectors of the optical flow image; and determining the weight coefficient set of each human joint based on the first-type weight coefficient set and the second-type weight coefficient set.

In this embodiment of this application, the to-be-processed image and the optical flow image are obtained from the to-be-processed video, and the pose is estimated based on weight coefficient sets obtained based on the to-be-processed image and the optical flow image, so that pose estimation accuracy can be improved.

Optionally, in an embodiment, the determining the weight coefficient set of each human joint based on the first-type weight coefficient set and the second-type weight coefficient set includes: weighting the first-type weight coefficient set and the second-type weight coefficient set to obtain the weight coefficient set of each human joint.

In this application, the first-type weight coefficient set and the second-type weight coefficient set are weighted, weights can be determined properly based on significance of the first image and the optical flow image to the pose estimation, so that the pose can be better estimated based on the obtained weight coefficient set of each human joint.

Figure 7:
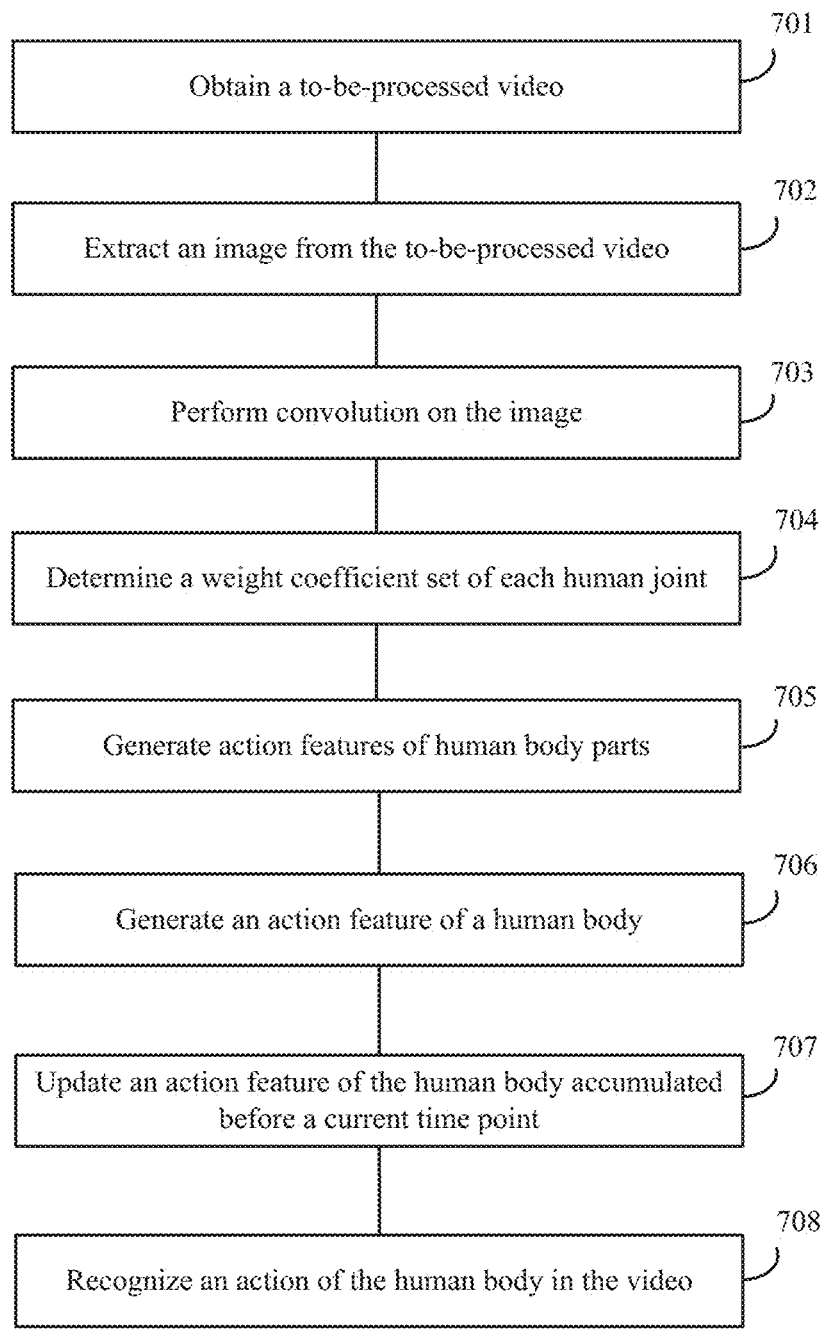
FIG. 7 is a schematic flowchart of an action recognition method according to an embodiment of this application.

It should be understood that, the method shown in FIG. 7 can be used not only for action recognition, but also for pose estimation for the human body in the video. Specifically, after the optical flow image is processed by using the method shown in FIG. 7 in the same way as processing an image, corresponding weight values in weight coefficient sets that are of each human joint and that are obtained based on the optical flow image and the to-be-processed image may be averaged, and then a location that has a largest weight coefficient in an averaged weight coefficient set is selected as an estimated location of the human joint. Subsequently, locations of other human joints are estimated in the same way, and the locations of the joints are connected, to estimate the pose of the human body.

Possible application scenarios of the action recognition method and the pose estimation method in the embodiments of this application are described below.

The action recognition method and the pose estimation method in the embodiments of this application are applicable to the following several scenarios.

Scenario 1: Pedestrian Behavior Analysis and Warning System

In an autonomous driving system (ADS) or an advanced driving assistant system (ADAS), avoidance of collisions with pedestrians is very important. A general method for resolving this problem is to recognize a pedestrian on a road and calculate a distance between the pedestrian and a vehicle to avoid a collision with the pedestrian. However, the collision with the pedestrian cannot be well avoided by simply calculating the distance between the pedestrian and the vehicle. The action recognition method in this application is applicable to a pedestrian behavior analysis and warning system. By using this method, an action type of the pedestrian is recognized, the action type of the pedestrian is obtained, and then a level of a threat to driving can be analyzed based on the action type of the pedestrian. For example, a pedestrian who is walking is less likely to be a threat to driving, and a pedestrian who is running or watching a mobile phone is more likely to be a threat to driving. Behavior of a relatively high level of a threat to driving is recognized, so that a warning can be raised or a corresponding measure can be taken beforehand.

Scenario 2: Dangerous Driving Behavior Reminder System

Many traffic accidents are caused by driver's negligence, such as driving while watching a mobile phone or driving while engaging in other dangerous behavior. The action recognition method in this application is applicable to a dangerous driving behavior reminder system. By using this method, dangerous driving behavior can be discovered and a warning is raised in time to reduce incidence of traffic accidents.

Figure 9:
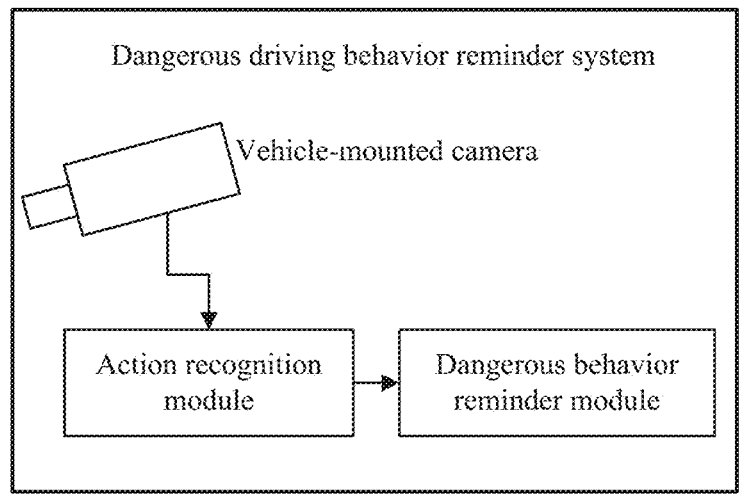
FIG. 9 is a schematic block diagram of a dangerous driving behavior reminder system.

As shown in FIG. 9, a dangerous driving behavior reminder system includes a vehicle-mounted camera, an action recognition module, and a dangerous behavior reminder module. The dangerous driving behavior reminder system shown in FIG. 9 is applicable to an ADAS. The dangerous driving behavior reminder system uses the vehicle-mounted camera to collect a video of a driver, and uses the action recognition module (the action recognition module may specifically use the action recognition method in the embodiments of this application to recognize an action of the driver) to recognize the action of the driver, such as normal driving or watching a mobile phone. When an action of the driver poses a threat to driving, the dangerous behavior reminder module warns the driver.

Scenario 3: Man-Machine Interaction System

In a man-machine interaction system, a video of a player may be processed by using the action recognition method and the pose estimation method in the embodiments of this application, so that an action (such as attack or defense) and a pose (locations of main human joints) of a human body are recognized. Subsequently, the man-machine interaction system may perform a corresponding operation (such as attack or defense) based on the recognized action, and based on the recognized pose, display, on a screen, a character who takes the same action as the player, thereby improving man-machine interaction experience.

Scenario 4: Dangerous Behavior Recognition System in Safe-City Construction

Figure 10:
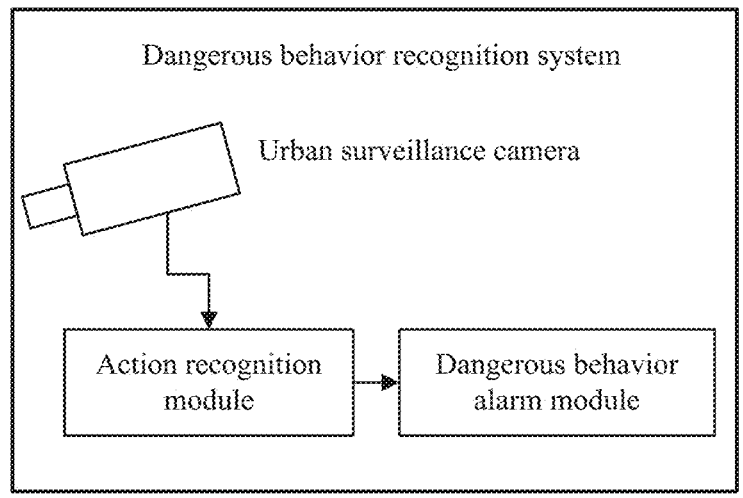
FIG. 10 is a schematic block diagram of a dangerous behavior recognition system.

As shown in FIG. 10, a dangerous behavior recognition system in safe-city construction may include an urban surveillance camera, an action recognition module, and a dangerous behavior alarm module. The dangerous behavior recognition system uses the urban surveillance camera to collect a video, and uses the action recognition module (the action recognition module may specifically use the action recognition method in the embodiments of this application to recognize an action of a person) to recognize the action of the person in the surveillance video. When the person in the surveillance video shows dangerous behavior (such as robbery, murder, or fighting), the danger alarm module sends alarm information to a related department.

It should be understood that, the action recognition method and the pose estimation method in the embodiments of this application is applicable to not only the foregoing scenarios 1 to 4, but also other scenarios in which action recognition or pose estimation needs to be performed for a human body in a video.

The action recognition method and the pose estimation method in the embodiments of this application are described in detail above with reference to FIG. 1 to FIG. 10, and an apparatus in the embodiments of this application is described below with reference to FIG. 11 to FIG. 19. It should be understood that, an action recognition apparatus 1100 to an action recognition apparatus 1400 shown in FIG. 11 to FIG. 14 can perform the action recognition method in the embodiments of this application, and a pose estimation apparatus 1500 to a pose estimation apparatus 1800 shown in FIG. 15 to FIG. 18 can perform the pose estimation method in the embodiments of this application. An action recognition and pose estimation apparatus 1900 shown in FIG. 19 can perform both the action recognition method in the embodiments of this application and the pose estimation method in the embodiments of this application.

Figure 11:
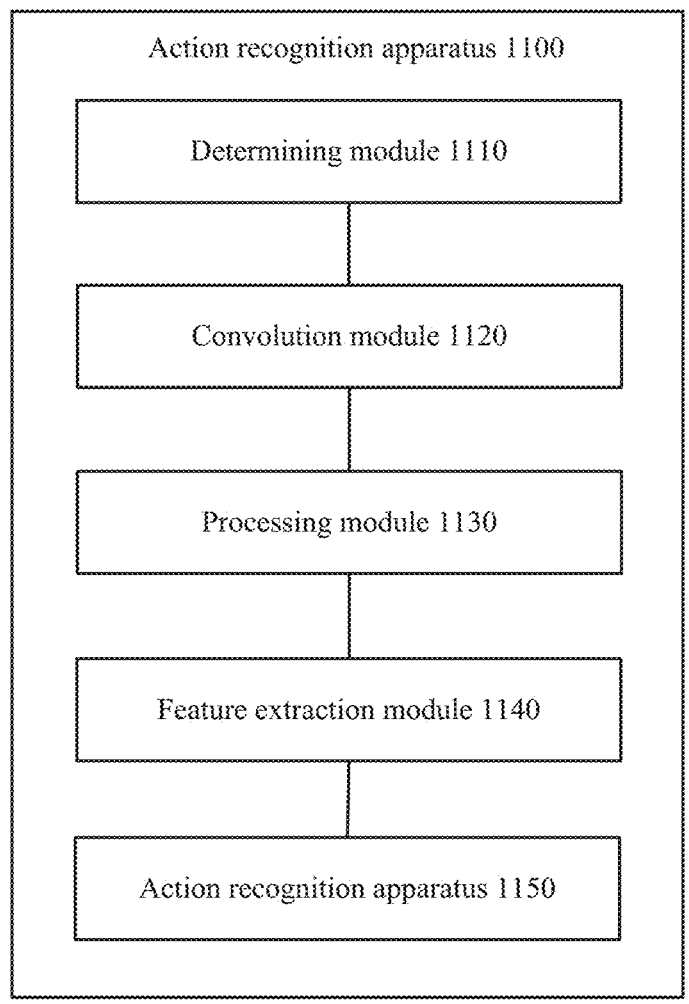
FIG. 11 is a schematic block diagram of an action recognition apparatus according to an embodiment of this application.

FIG. 11 is a schematic block diagram of an action recognition apparatus according to an embodiment of this application. The action recognition apparatus 1100 in FIG. 11 includes:

a determining module 1110, configured to determine a to-be-processed video, where the to-be-processed video is a video that includes images of a human body, where the determining module 1110 is further configured to determine a to-be-processed image based on the to-be-processed video, where the to-be-processed image is at least one of a first image, or an optical flow image generated based on a plurality of frames of images in the to-be-processed video, where the first image is any frame of image in the to-be-processed video, or the first image is a composite image of a plurality of frames of images in the to-be-processed video;

a convolution module 1120, configured to perform convolution on the to-be-processed image to obtain a plurality of eigenvectors, where the plurality of eigenvectors are respectively used to denote features of different locations in the to-be-processed image;

a processing module 1130, configured to determine a weight coefficient set of each human joint of the human body based on the plurality of eigenvectors, where the weight coefficient set of the human joint includes a weight coefficient of each of the plurality of eigenvectors for the human joint, a weight coefficient of a first-type eigenvector is greater than or equal to a weight coefficient of a second-type eigenvector, a distance between a corresponding location of the first-type eigenvector in the to-be-processed image and a corresponding location of the human joint in the to-be-processed image is a first distance, a distance between a corresponding location of the second-type eigenvector in the to-be-processed image and the corresponding location of the human joint in the to-be-processed image is a second distance, the first distance is less than or equal to the second distance, there are a plurality of human joints, and each human joint corresponds to one weight coefficient set;

a feature extraction module 1140, configured to weight the plurality of eigenvectors based on the weight coefficient set of each human joint to obtain an action feature of each human joint, where the feature extraction module 1140 is further configured to determine an action feature of the human body based on the action feature of each human joint: and an action recognition module 1150, configured to determine an action type of the human body based on the action feature of the human body.

In this application, the weight coefficient of the first-type eigenvector is greater than or equal to the weight coefficient of the second-type eigenvector, and the distance between the corresponding location of the first-type eigenvector in the to-be-processed image and the corresponding location of the human joint in the to-be-processed image is less than or equal to the distance between the corresponding location of the second-type eigenvector in the to-be-processed image and the corresponding location of the human joint in the to-be-processed image. Therefore, in this application, a weight coefficient of an eigenvector corresponding to a region closer to the human joint is larger. In this way, a feature closely related to an action in the to-be-processed image can occupy a relatively large proportion in action recognition, and a feature less related to the action in the to-be-processed image can occupy a relatively small proportion in the action recognition. In the action recognition according to this application, significance of features of different regions in the to-be-processed image to the action recognition is taken into full account, so that a more robust action feature can be obtained, thereby improving action recognition accuracy.

Optionally, in an embodiment, the processing module 1130 is specifically configured to:

determine the weight coefficient set of each human joint based on the plurality of eigenvectors and cumulative action information of the human body, where the cumulative action information of the human body is used to indicate an action feature of the human body accumulated before a current time point.

Optionally, in an embodiment, the feature extraction module 1140 is specifically configured to:

weight or combine action features of all the human joints to obtain the action feature of the human body.

Optionally, in an embodiment, the feature extraction module 1140 is specifically configured to:

weight or combine action features of all the human joints to obtain action features of human body parts, where the human body includes a plurality of human body parts, and each human body part includes at least one human joint; and weight or combine the action features of the human body parts to obtain the action feature of the human body.

Optionally, in an embodiment, the to-be-processed image includes the first image and the optical flow image, and the convolution module 1120 is specifically configured to:

perform convolution on the first image to obtain a plurality of eigenvectors of the first image; and perform convolution on the optical flow image to obtain a plurality of eigenvectors of the optical flow image.

The processing module 1130 is specifically configured to:

determine a first-type weight coefficient set of each human joint based on the plurality of eigenvectors of the first image; and determine a second-type weight coefficient set of each human joint based on the plurality of eigenvectors of the optical flow image.

The feature extraction module 1140 is specifically configured to:

weight the plurality of eigenvectors of the first image based on the first-type weight coefficient set to obtain a first-type action feature of each human joint;

weight the plurality of eigenvectors of the optical flow image based on the second-type weight coefficient set to obtain a second-type action feature of each human joint; and weight or combine first-type action features of all the human joints and second-type action features of all the human joints to obtain the action feature of the human body.

Figure 12:
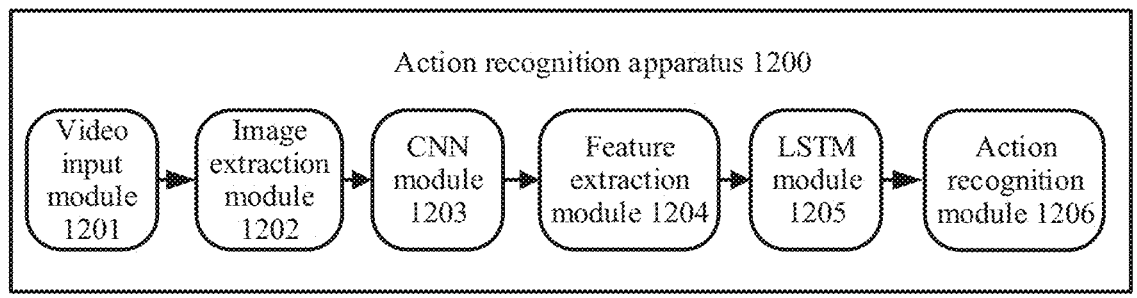
FIG. 12 is a schematic block diagram of an action recognition apparatus according to an embodiment of this application.

FIG. 12 is a schematic block diagram of an action recognition apparatus according to an embodiment of this application. The action recognition apparatus 1200 shown in FIG. 12 includes: a video input module 1201, an image extraction module 1202, a CNN module 1203, a feature extraction module 1204, an LSTM module 1205, and an action recognition module 1206.

Figure 13:
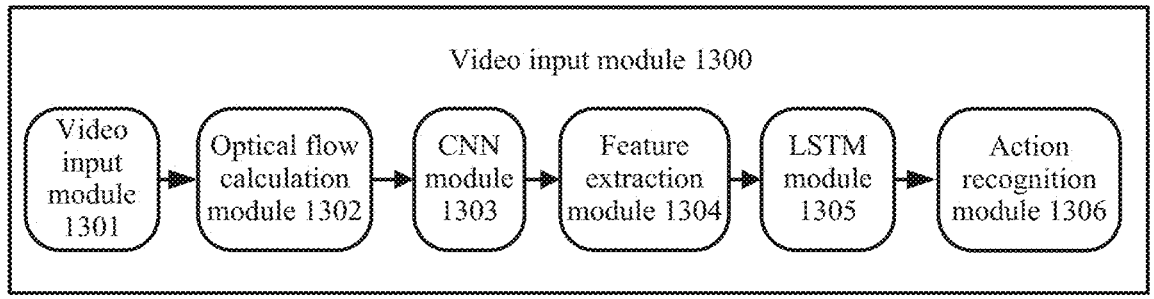
FIG. 13 is a schematic block diagram of an action recognition apparatus according to an embodiment of this application.

FIG. 13 is a schematic block diagram of an action recognition apparatus according to an embodiment of this application.

The action recognition apparatus 1300 shown in FIG. 13 includes: a video input module 1301, an optical flow calculation module 1302, a CNN module 1303, a feature extraction module 1304, an LSTM module 1305, and an action recognition module 1306.

Figure 14:
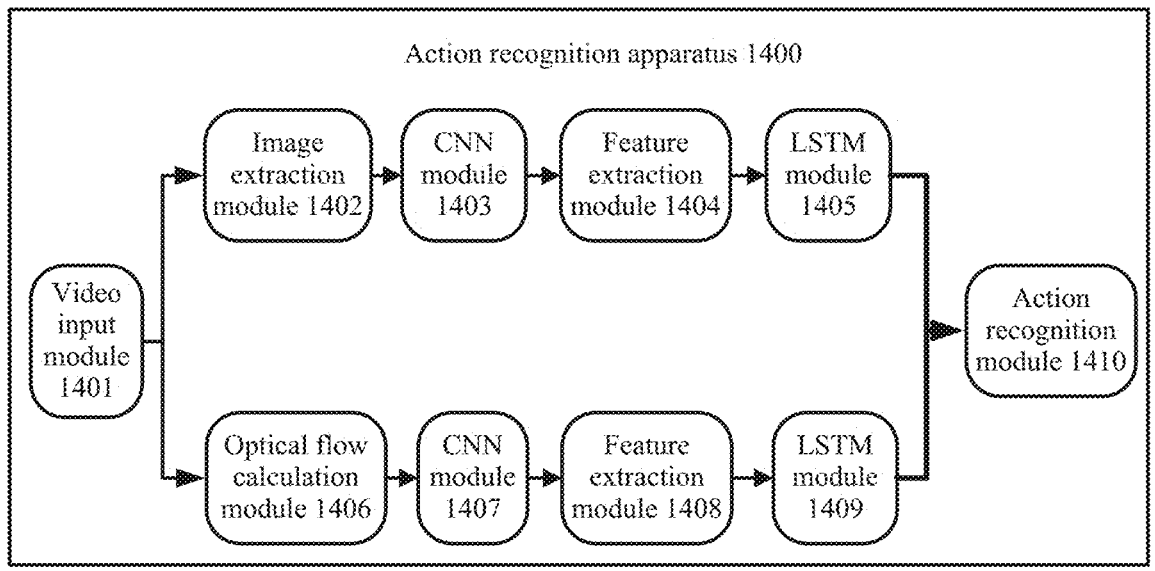
FIG. 14 is a schematic block diagram of an action recognition apparatus according to an embodiment of this application.

FIG. 14 is a schematic block diagram of an action recognition apparatus according to an embodiment of this application.

The action recognition apparatus 1400 shown in FIG. 14 includes: a video input module 1401, an image extraction module 1402, a CNN module 1403, a feature extraction module 1404, an LSTM module 1405, an optical flow calculation module 1406, a CNN module 1407, a feature extraction module 1408, an LSTM module 1409, and an action recognition module 1410.

The action recognition apparatus 1200 in FIG. 12 recognizes a human body action in a video based on a specific frame of image in the to-be-processed video, and the action recognition apparatus 1300 in FIG. 13 recognizes a human body action in a video based on an optical flow image. Herein, the optical flow image is an image generated based on a plurality of frames of images in the to-be-processed video.

In addition, for the action recognition apparatus 1400 in FIG. 14, the apparatus 1400 extracts a feature from an image extracted from a to-be-processed video, and also extracts a feature from an optical flow image, and finally, the action recognition module 1410 recognizes an action based on the feature extracted from the image extracted from the to-be-processed video and the feature extracted from the optical flow image. In this way, both spatial characteristics of the human body action in the to-be-processed video and time change characteristics of the human body action in the to-be-processed video are taken into account, so that action recognition accuracy can be improved.

It should be understood that, the action recognition apparatus 1100, the action recognition apparatus 1200, the action recognition apparatus 1300, and the action recognition apparatus 1400 are applicable to the scenarios 1 to 4 described above, and are configured to recognize a human body action in a video. Specifically, the action recognition apparatuses 1100 to 1400 may be devices in the systems in the foregoing scenarios 1 to 4, and are configured to recognize a human body action in a video in corresponding scenarios.

Figure 15:
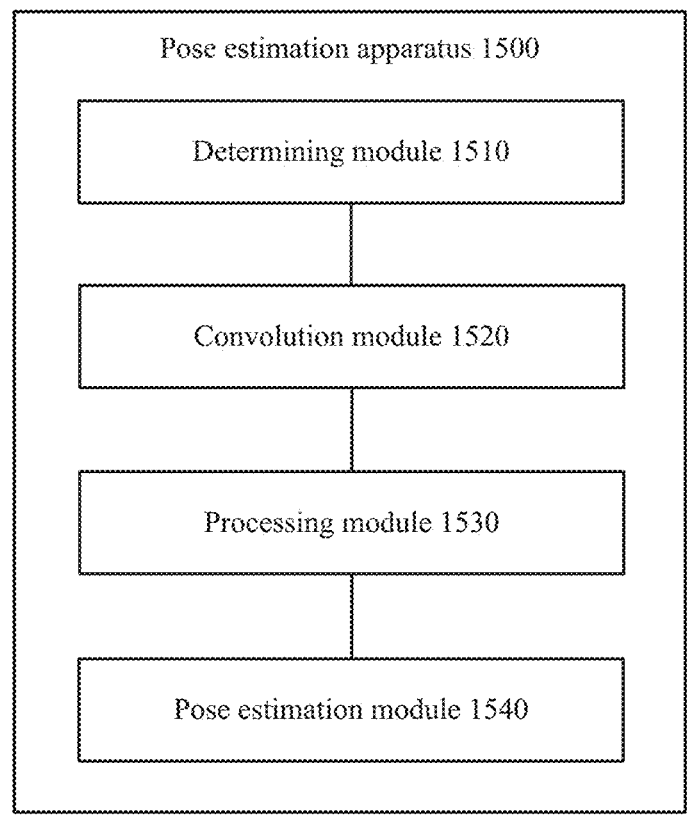
FIG. 15 is a schematic block diagram of a pose estimation apparatus according to an embodiment of this application.

FIG. 15 is a schematic block diagram of a pose estimation apparatus according to an embodiment of this application. The pose estimation apparatus 1500 in FIG. 15 includes:

a determining module 1510, configured to determine a to-be-processed video, where the to-be-processed video is a video that includes images of a human body, where the determining module 1510 is further configured to determine a to-be-processed image based on the to-be-processed video, where the to-be-processed image is at least one of a first image, or an optical flow image generated based on a plurality of frames of images in the to-be-processed video, where the first image is any frame of image in the to-be-processed video, or the first image is a composite image of a plurality of frames of images in the to-be-processed video;

a convolution module 1520, configured to perform convolution on the to-be-processed image to obtain a plurality of eigenvectors, where the plurality of eigenvectors are respectively used to denote features of different locations in the to-be-processed image;

a processing module 1530, configured to determine a weight coefficient set of each human joint of the human body based on the plurality of eigenvectors, where the weight coefficient set of the human joint includes a weight coefficient of each of the plurality of eigenvectors for the human joint, a weight coefficient of a first-type eigenvector is greater than or equal to a weight coefficient of a second-type eigenvector, a distance between a corresponding location of the first-type eigenvector in the to-be-processed image and a corresponding location of the human joint in the to-be-processed image is a first distance, a distance between a corresponding location of the second-type eigenvector in the to-be-processed image and the corresponding location of the human joint in the to-be-processed image is a second distance, the first distance is less than or equal to the second distance, there are a plurality of human joints, and each human joint corresponds to one weight coefficient set; and a pose estimation module 1540, configured to determine a corresponding region of a first eigenvector of the plurality of eigenvectors in the to-be-processed image as a location of the human joint, where a weight coefficient of the first eigenvector is a first weight coefficient, and the first weight coefficient is a weight coefficient greater than a preset threshold in the weight coefficient set of the human joint, where the pose estimation module 1540 is further configured to determine a pose of the human body based on the location of the human joint.

In this application, the pose of the human body in the video is estimated based on the weight set of each human joint, so that a feature closely related to an action in the to-be-processed video can occupy a relatively large proportion. Compared with the existing solution in which all features are extracted from an image in a to-be-processed video to estimate a pose, the solution in this application can more accurately determine the pose of the human body in the video.

Optionally, in an embodiment, the processing module 1530 is specifically configured to:

determine the weight coefficient set of each human joint based on the plurality of eigenvectors and cumulative action information of the human body, where the cumulative action information of the human body is used to indicate an action feature of the human body accumulated before a current time point.

Optionally, in an embodiment, the to-be-processed image includes the first image and the optical flow image, and the convolution module 1520 is specifically configured to:

perform convolution on the first image to obtain a plurality of eigenvectors of the first image; and perform convolution on the optical flow image to obtain a plurality of eigenvectors of the optical flow image.

The processing module 1530 is specifically configured to:

determine a first-type weight coefficient set of each human joint based on the plurality of eigenvectors of the first image;

determine a second-type weight coefficient set of each human joint based on the plurality of eigenvectors of the optical flow image; and determine the weight coefficient set of each human joint based on the first-type weight coefficient set and the second-type weight coefficient set.

Optionally, in an embodiment, the processing module 1530 is specifically configured to weight the first-type weight coefficient set and the second-type weight coefficient set to obtain the weight coefficient set of each human joint.

Figure 16:
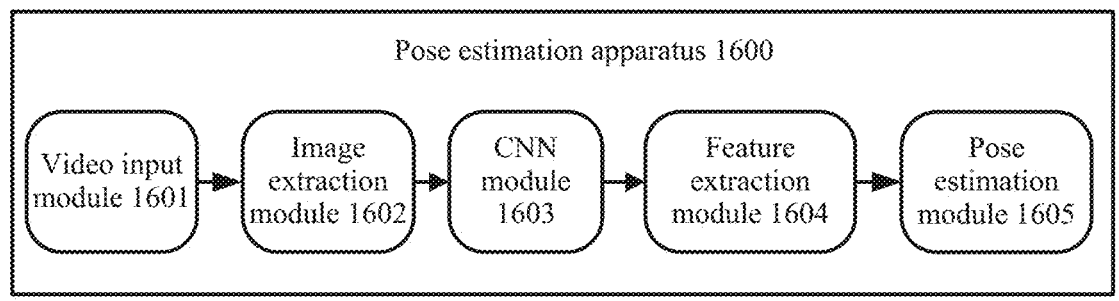
FIG. 16 is a schematic block diagram of a pose estimation apparatus according to an embodiment of this application.

FIG. 16 is a schematic block diagram of a pose estimation apparatus according to an embodiment of this application.

The pose estimation apparatus 1600 in FIG. 16 includes: a video input module 1601, an image extraction module 1602, a CNN module 1603, a feature extraction module 1604, and a pose estimation module 1605.

Figure 17:
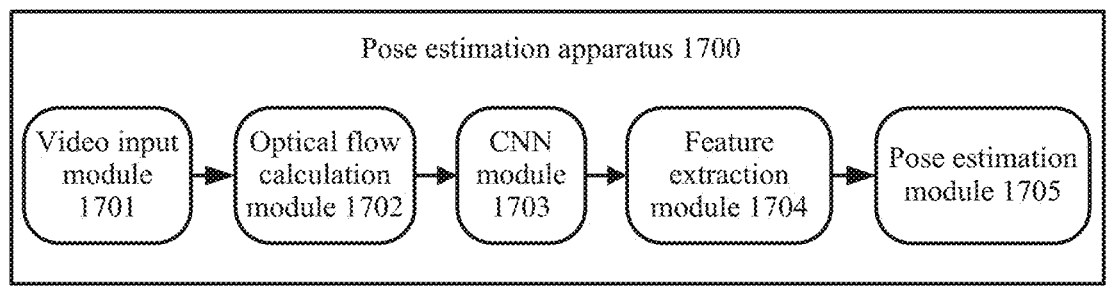
FIG. 17 is a schematic block diagram of a pose estimation apparatus according to an embodiment of this application.

FIG. 17 is a schematic block diagram of a pose estimation apparatus according to an embodiment of this application.

The pose estimation apparatus 1700 in FIG. 17 includes: a video input module 1701, an optical flow calculation module 1702, a CNN module 1703, a feature extraction module 1704, and a pose estimation module 1705.

Figure 18:
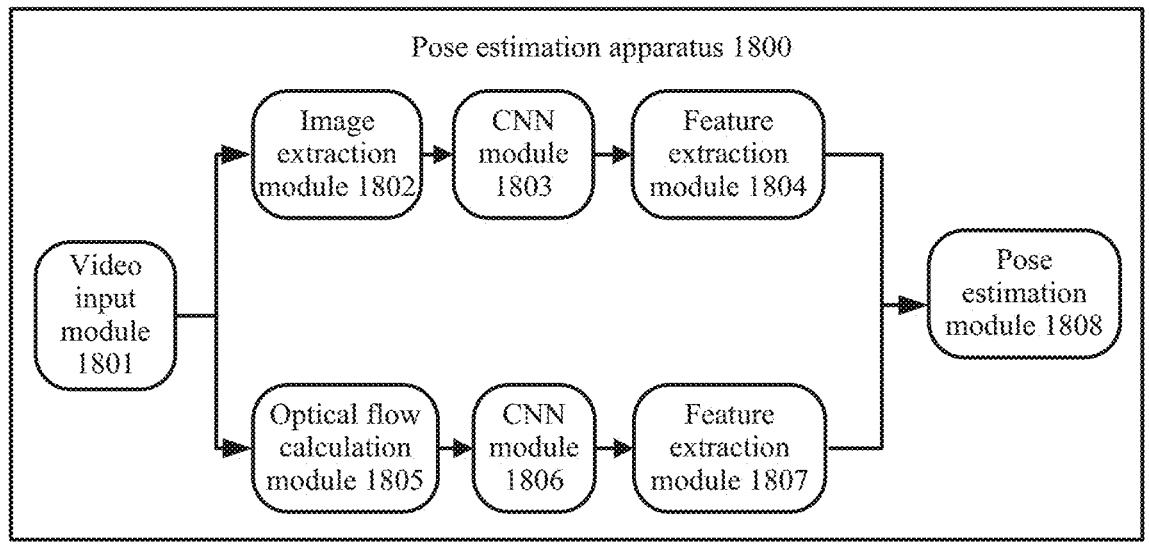
FIG. 18 is a schematic block diagram of a pose estimation apparatus according to an embodiment of this application.

FIG. 18 is a schematic block diagram of a pose estimation apparatus according to an embodiment of this application.

The pose estimation apparatus 1800 shown in FIG. 18 includes: a video input module 1801, an image extraction module 1802, a CNN module 1803, a feature extraction module 1804, an optical flow calculation module 1805, a CNN module 1806, a feature extraction module 1807, and a pose estimation module 1808.

The pose estimation apparatus 1600 in FIG. 16 estimates a human body pose in a video based on a specific frame of image in the to-be-processed video, and the pose estimation apparatus 1700 in FIG. 17 estimates a human body pose in a video based on an optical flow image. Herein, the optical flow image is an image generated based on a plurality of frames of images in the to-be-processed video.

In addition, for the pose estimation apparatus 1800 in FIG. 18, the apparatus 1800 extracts a feature from an image extracted from a to-be-processed video, and also extracts a feature from an optical flow image, and finally, the pose estimation module 1808 estimates a pose based on the feature extracted from the image extracted from the to-be-processed video and the feature extracted from the optical flow image. In this way, both spatial characteristics of a human body action in the to-be-processed video and time change characteristics of the human body action in the to-be-processed video are taken into account, so that pose estimation accuracy can be improved.

It should be understood that, the pose estimation apparatus 1500, the pose estimation apparatus 1600, the pose estimation apparatus 1700, and the pose estimation apparatus 1800 are applicable to the scenarios 1 to 4 described above, and are configured to estimate a human body pose in a video. Specifically, the pose estimation apparatuses 1500 to 1800 may be devices in the systems in the foregoing scenarios 1 to 4, and are configured to estimate a human body pose in a video in corresponding scenarios.

Figure 19:
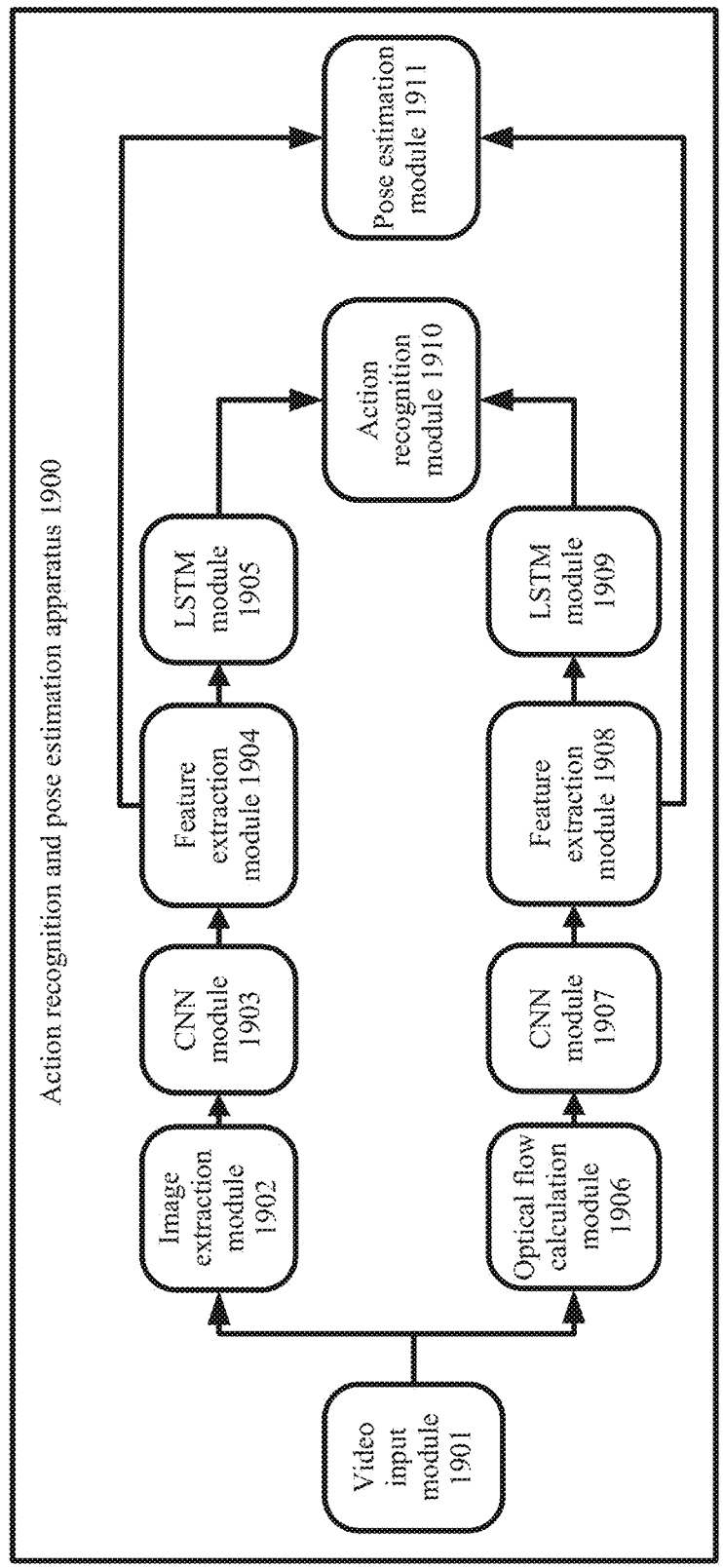
FIG. 19 is a schematic block diagram of an action recognition and pose estimation apparatus according to an embodiment of this application.

FIG. 19 is a schematic block diagram of an action recognition and pose estimation apparatus according to an embodiment of this application. The action recognition and pose estimation apparatus 1900 in FIG. 19 includes: a video input module 1901, an image extraction module 1902, a CNN module 1903, a feature extraction module 1904, an LSTM module 1905, an optical flow calculation module 1906, a CNN module 1907, a feature extraction module 1908, an LSTM module 1909, an action recognition module 1910, and a pose estimation module 1911.

The action recognition and pose estimation apparatus 1900 in FIG. 19 extracts a feature from an image extracted from a to-be-processed video, and also extracts a feature from an optical flow image. In addition, the pose estimation apparatus 1900 can perform both dynamic estimation and pose estimation, and estimate a pose of an entity in the video while recognizing an action of a human body in the video.

This application provides an action recognition apparatus. The apparatus includes a storage medium and a central processing unit. The storage medium may be a non-volatile storage medium, and the storage medium stores a computer-executable program. The central processing unit is connected to the non-volatile storage medium, and executes the computer-executable program to implement the action recognition method in the embodiments of this application.

This application provides a pose estimation apparatus. The apparatus includes a storage medium and a central processing unit. The storage medium may be a non-volatile storage medium, and the storage medium stores a computer-executable program. The central processing unit is connected to the non-volatile storage medium, and executes the computer-executable program to implement the pose estimation method in the embodiments of this application.

This application provides a chip. The chip includes a processor and a communications interface. The communications interface is configured to communicate with an external device, and the processor is configured to perform the action recognition method in the embodiments of this application.

Optionally, in an implementation, the chip may further include a memory. The memory stores an instruction, and the processor is configured to execute the instruction stored in the memory. When the instruction is executed, the processor is configured to perform the action recognition method in the embodiments of this application.

This application provides a chip. The chip includes a processor and a communications interface. The communications interface is configured to communicate with an external device, and the processor is configured to perform the pose estimation method in the embodiments of this application.

Optionally, in an implementation, the chip may further include a memory. The memory stores an instruction, and the processor is configured to execute the instruction stored in the memory. When the instruction is executed, the processor is configured to perform the pose estimation method in the embodiments of this application.

This application provides a computer-readable storage medium. The computer-readable storage medium stores program code to be executed by a device, and the program code includes an instruction for performing the action recognition method in the embodiments of this application.

This application provides a computer-readable storage medium. The computer-readable storage medium is configured to store program code to be executed by a device, and the program code includes an instruction for performing the pose estimation method in the embodiments of this application.

A person of ordinary skill in the art may be aware that, units and algorithm steps in the examples described with reference to the embodiments disclosed in this specification may be implemented by electronic hardware or a combination of computer software and electronic hardware. Whether the functions are performed by hardware or software depends on particular applications and design constraints of the technical solutions. A person skilled in the art may use different methods to implement the described functions for each particular application, but it should not be considered that the implementation goes beyond the scope of this application.

It may be clearly understood by a person skilled in the art that, for the purpose of convenient and brief description, for a detailed working process of the foregoing system, apparatus, and unit, reference may be made to a corresponding process in the foregoing method embodiments, and details are not described herein again.

In the several embodiments provided in this application, it should be understood that the disclosed system, apparatus, and method may be implemented in other manners. For example, the described apparatus embodiment is merely an example. For example, the unit division is merely logical function division and may be other division in actual implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electrical, mechanical, or other forms.

The units described as separate parts may or may not be physically separate, and parts displayed as units may or may not be physical units, that is, may be located in one position, or may be distributed on a plurality of network units. Some or all of the units may be selected based on actual requirements to achieve the objectives of the solutions of the embodiments.

In addition, functional units in the embodiments of this application may be integrated into one processing unit, or each of the units may exist alone physically, or two or more units may be integrated into one unit.

When the functions are implemented in the form of a software functional unit and sold or used as an independent product, the functions may be stored in a computer-readable storage medium. Based on such an understanding, the technical solutions of this application essentially, or the part contributing to the prior art, or some of the technical solutions may be implemented in a form of a software product. The computer software product is stored in a storage medium, and includes several instructions for instructing a computer device (which may be a personal computer, a server, a network device, or the like) to perform all or some of the steps of the methods described in the embodiments of this application. The foregoing storage medium includes: any medium that can store program code, such as a USB flash drive, a removable hard disk, a read-only memory (ROM), a random access memory (RAM), a magnetic disk, or an optical disc.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. An action recognition method, comprising:
identifying a video to be processed that comprises images of a human body;
identifying at least one image to be processed, wherein the at least one image is at least one of an optical flow image generated based on a plurality of frames of images in the video, or a composite image of one or more frames of images in the video;
performing convolution on the at least one image to obtain a plurality of eigenvectors, wherein the plurality of eigenvectors indicate a plurality of features of different locations in the at least one image;
determining a weight coefficient set of each of a plurality of human joints of the human body based on the plurality of eigenvectors, wherein the weight coefficient set comprises a weight coefficient of each of the plurality of eigenvectors for the human joint a distance between a corresponding location of the first-type eigenvector in the at least one image and a corresponding location of the human joint in the at least one image is a first distance, a distance between a corresponding location of the second-type eigenvector in the at least one image and the corresponding location of the human joint in the at least one image is a second distance, the first distance is less than or equal to the second distance;

weighting the plurality of eigenvectors based on the weight coefficient set to obtain an action feature of each of a plurality of human joints;

determining an action feature of the human body based on the action feature of each of the human joints; and determining an action type of the human body based on the action feature of the human body.

2. The method according to claim 1, wherein the weight coefficient set of each of the human joints is further determined based on cumulative action information of the human body, wherein the cumulative action information of the human body indicates an action feature of the human body accumulated before a current time point.

3. The method according to claim 1, wherein the action feature of the human body is determined by weighting or combining the action feature of the plurality of human joints.

4. The method according to claim 1, wherein the action feature of the human body is determined by weighting or combining action feature of each of a plurality of human parts of the human body, and wherein the action feature of each of the plurality of human parts is determined by weighting or combining the action feature of each of the plurality of human joints.

5. The method according to claim 1, wherein the at least one image comprises the composite image and the optical flow image, and the performing convolution on the at least one image to obtain a plurality of eigenvectors comprises:

performing convolution on the composite image to obtain a plurality of eigenvectors of the composite image; and performing convolution on the optical flow image to obtain a plurality of eigenvectors of the optical flow image;

the determining the weight coefficient set comprises:

determining a first-type weight coefficient set of each of the plurality of human joints based on the plurality of eigenvectors of the composite image; and determining a second-type weight coefficient set of each of the plurality of human joints based on the plurality of eigenvectors of the optical flow image;

the weighting the plurality of eigenvectors based on the weight coefficient set comprises:

weighting the plurality of eigenvectors of the composite image based on the first-type weight coefficient set to obtain a first-type action feature of each of the plurality of human joints; and weighting the plurality of eigenvectors of the optical flow image based on the second-type weight coefficient set to obtain a second-type action feature of each of the plurality of human joints; and wherein the action feature of the human body is determined by weighting or combining first-type action features of the plurality of human joints and second-type action features of the plurality of human joints.

6. A pose estimation method, comprising:

identifying a video to be processed that comprises images of a human body;

identifying at least one image to be processed, wherein the at least one image is at least one of an optical flow image generated based on a plurality of frames of images in the video, or a composite image of one or more frames of images in the video;

performing convolution on the at least one image to obtain a plurality of eigenvectors, wherein the plurality of eigenvectors indicate a plurality of features of different locations in the at least one image;

determining a weight coefficient set of each of a plurality of human joints of the human body based on the plurality of eigenvectors, wherein the weight coefficient set comprises a weight coefficient of each of the plurality of eigenvectors for the human joint, a weight coefficient of a first-type eigenvector is greater than or equal to a weight coefficient of a second-type eigenvector, a distance between a corresponding location of the first-type eigenvector in the at least one image and a corresponding location of the human joint in the at least one image is a first distance, a distance between a corresponding location of the second-type eigenvector in the at least one image and the corresponding location of the human joint in the at least one image is a second distance, the first distance is less than or equal to the second distance;

determining a corresponding region of a first eigenvector of the plurality of eigenvectors in the at least one image as a location of the human joint, wherein a weight coefficient of the first eigenvector is a first weight coefficient, and the first weight coefficient is a weight coefficient greater than a preset threshold in the weight coefficient set of the human joint; and determining a pose of the human body based on the location of the human joint.

7. The method according to claim 6, wherein the weight coefficient set of each of the human joints is further determined based on cumulative action information of the human body, wherein the cumulative action information of the human body indicates an action feature of the human body accumulated before a current time point.

8. The method according to claim 6, wherein the at least one image comprises the composite image and the optical flow image, and the performing convolution on the at least one image to obtain a plurality of eigenvectors comprises:

performing convolution on the composite image to obtain a plurality of eigenvectors of the composite image; and performing convolution on the optical flow image to obtain a plurality of eigenvectors of the optical flow image;

the determining the weight coefficient set comprises:

determining a first-type weight coefficient set of each of the plurality of human joints based on the plurality of eigenvectors of the composite image; and determining a second-type weight coefficient set of each of the plurality of human joints based on the plurality of eigenvectors of the optical flow image; and determining the weight coefficient set of each human joint based on the first-type weight coefficient set and the second-type weight coefficient set.

9. The method according to claim 8, wherein the weight coefficient set of each human joint is determined based on weighting the first-type weight coefficient set and the second-type weight coefficient set.

10. An action recognition device, comprising at least one processor and a non-transitory medium storing program instructions, wherein the at least one processor, by executing the program instructions, causes the action recognition device to:

identifying a video to be processed that comprises images of a human body, wherein identifying at least one image to be processed, wherein the at least one image is at least one of an optical flow image generated based on a plurality of frames of images in the video, or a composite image of one or more frames of images in the video;

perform convolution on the at least one image to obtain a plurality of eigenvectors, wherein the plurality of eigenvectors indicate a plurality of features of different locations in the at least one image;

determine a weight coefficient set of each of a plurality of human joints of the human body based on the plurality of eigenvectors, wherein the weight coefficient set comprises a weight coefficient of each of the plurality of eigenvectors for the human joint, a weight coefficient of a first-type eigenvector is greater than or equal to a weight coefficient of a second-type eigenvector, a distance between a corresponding location of the first-type eigenvector in the at least one image and a corresponding location of the human joint in the at least one image is a first distance, a distance between a corresponding location of the second-type eigenvector in the at least one image and the corresponding location of the human joint in the at least one image is a second distance, the first distance is less than or equal to the second distance;

weight the plurality of eigenvectors based on the weight coefficient set to obtain an action feature of each of the plurality of human joints, wherein determine an action feature of the human body based on the action feature of each of the human joints; and determine an action type of the human body based on the action feature of the human body.

11. The action recognition device according to claim 10, wherein the weight coefficient set of each of the human joints is further determined based on cumulative action information of the human body, wherein the cumulative action information of the human body indicates an action feature of the human body accumulated before a current time point.

12. The action recognition device according to claim 10, wherein the at least one processor further causes the action recognition device to:

weight or combine the action feature of the plurality of human joints.

13. The action recognition device according to claim 10, wherein the action feature of the human body is determined by weighting or combining action feature of each of a plurality of human parts of the human body, and wherein the action feature of each of the plurality of human parts is determined by weighting or combining the action feature of each of the plurality of human joints.

14. The action recognition device according to claim 10, wherein the at least one image comprises the composite image and the optical flow image, and the at least one processor further causes the action recognition device to:

perform convolution on the composite image to obtain a plurality of eigenvectors of the composite image; and perform convolution on the optical flow image to obtain a plurality of eigenvectors of the optical flow image;

the processor is specifically configured to:

determine a first-type weight coefficient set of each of the plurality of human joints based on the plurality of eigenvectors of the composite image; and determine a second-type weight coefficient set of each of the plurality of human joints based on the plurality of eigenvectors of the optical flow image; and the processor is specifically configured to:

weight the plurality of eigenvectors of the composite image based on the first-type weight coefficient set to obtain a first-type action feature of each of the plurality of human joints;

weight the plurality of eigenvectors of the optical flow image based on the second-type weight coefficient set to obtain a second-type action feature of each of the plurality of human joints; and wherein weight or combine first-type action features of the plurality of human joints and second-type action features of the plurality of human joints.

15. A pose estimation device, comprising at least one processor and a non-transitory medium storing program instructions, wherein the at least one processor, by executing the program instructions, causes the pose estimation device to:

identifying a video to be processed that comprises images of a human body, wherein identifying at least one image to be processed, wherein the at least one image is at least one of an optical flow image generated based on a plurality of frames of images in the video, or a composite image of one or more frames of images in the video;

perform convolution on the at least one image to obtain a plurality of eigenvectors, wherein the plurality of eigenvectors indicate a plurality of features of different locations in the at least one image;

determine a weight coefficient set of each of a plurality of human joints of the human body based on the plurality of eigenvectors, wherein the weight coefficient set comprises a weight coefficient of each of the plurality of eigenvectors for the human joint, a weight coefficient of a first-type eigenvector is greater than or equal to a weight coefficient of a second-type eigenvector, a distance between a corresponding location of the first-type eigenvector in the at least one image and a corresponding location of the human joint in the at least one image is a first distance, a distance between a corresponding location of the second-type eigenvector in the at least one image and the corresponding location of the human joint in the at least one image is a second distance, the first distance is less than or equal to the second distance;

determine a corresponding region of a first eigenvector of the plurality of eigenvectors in the at least one image as a location of the human joint, wherein a weight coefficient of the first eigenvector is a first weight coefficient, and the first weight coefficient is a weight coefficient greater than a preset threshold in the weight coefficient set of the human joint; and determine a pose of the human body based on the location of the human joint.

16. The pose estimation device according to claim 15, wherein the weight coefficient set of each of the human joints is further determined based on cumulative action information of the human body, wherein the cumulative action information of the human body indicates an action feature of the human body accumulated before a current time point.

17. The pose estimation device according to claim 15, wherein the at least one image comprises the composite image and the optical flow image, and the processor is specifically configured to:

perform convolution on the composite image to obtain a plurality of eigenvectors of the composite image; and perform convolution on the optical flow image to obtain a plurality of eigenvectors of the optical flow image; and the processor is specifically configured to:
determine a first-type weight coefficient set of each of the plurality of human joints based on the plurality of eigenvectors of the composite image;
determine a second-type weight coefficient set of each of the plurality of human joints based on the plurality of eigenvectors of the optical flow image; and
determine the weight coefficient set of each human joint based on the first-type weight coefficient set and the second-type weight coefficient set.

18. The pose estimation device according to claim 17, wherein the weight coefficient set of each human joint is determined based on weighting the first-type weight coefficient set and the second-type weight coefficient set.

\* \* \* \* \*